(12) United States Patent
Tang et al.

(10) Patent No.: US 7,074,604 B1
(45) Date of Patent: Jul. 11, 2006

(54) BIOPRODUCTION OF ASTAXANTHIN USING MUTANT CAROTENOID KETOLASE AND CAROTENOID HYDROXYLASE GENES

(75) Inventors: Xiao-Song Tang, Hockessin, DE (US); Qiong Cheng, Hockessin, DE (US); Joanne Y. Shyr, Newark, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/025,177

(22) Filed: Dec. 29, 2004

(51) Int. Cl.
*C12N 9/02* (2006.01)
*C12N 9/00* (2006.01)
*C12N 1/20* (2006.01)
*C12N 15/00* (2006.01)
*C07H 21/04* (2006.01)

(52) U.S. Cl. .................... 435/189; 435/69.1; 435/183; 435/252.3; 435/252.33; 435/858; 435/320.1; 536/23.2

(58) Field of Classification Search ............... 435/69.1, 435/183, 189, 252.3, 252.33, 320.1, 858; 536/23.2
See application file for complete search history.

(56) References Cited

U.S. PATENT DOCUMENTS

| | | | |
|---|---|---|---|
| 5,684,238 | A | 11/1997 | Ausich et al. |
| 5,811,273 | A | 9/1998 | Misawa et al. |
| 5,916,791 | A | 6/1999 | Hirschberg et al. |
| 5,965,795 | A | 10/1999 | Hirschberg et al. |
| 5,972,690 | A | 10/1999 | Misawa et al. |
| 6,218,599 | B1 | 4/2001 | Hirschberg et al. |
| 6,291,204 | B1 | 9/2001 | Pasamontes et al. |
| 6,677,134 | B1 | 1/2004 | Pasamontes et al. |
| 2002/0102631 | A1 | 8/2002 | Cunningham, Jr. et al. |
| 2002/0147371 | A1 | 10/2002 | Hohmann et al. |
| 2003/0100045 | A1 | 5/2003 | Cheng et al. |
| 2004/0268439 | A1 | 12/2004 | Cheng et al. |

FOREIGN PATENT DOCUMENTS

| | | |
|---|---|---|
| CN | 1380415 | 11/2002 |
| EP | 0393690 B1 | 10/1990 |
| FR | 2792335 A1 | 4/1999 |
| WO | WO 99/07867 | 2/1999 |
| WO | WO 00/61764 | 10/2000 |
| WO | WO 02/079395 A2 | 10/2002 |
| WO | WO 03/012056 A2 | 2/2003 |
| WO | WO 03/016503 A2 | 2/2003 |
| WO | WO 2004/029275 A1 | 4/2004 |

OTHER PUBLICATIONS

Nishida et al. Appl Environ Microbiol. Aug. 2005;71(8):4286-96.*
U.S. Appl. No. 60/577,970, filed Jun. 8, 2004, Cheng et al.
B. Hundle et al., Functional assignment of *Erwinia herbicola* Eho10 carotenoid genes expressed in *Escherichia coli*, Mol. Gen. Genet., vol. 245:406-416, 1994.
Yuhong Zhou et al., Random mutagenesis of gene-sized DNA molecules by use of PCR with Taq DNA polymerase, Nucleic Acids Res., vol. 19(21):6052, 1991.
Yasukazu Nakamura et al., Complete Genome Structure of *Gloeobacter violaceus* PCC 7421, a Cyanobacterium that Lacks Thylakoids (Supplement), DNA Res., vol. 10 (Suppl):181-201, 2003.
Gregory Armstrong, Carotenoid Genetics and Biochemistry, Elsevier Press, vol. 2:321-352, 1999.
Sabine Steiger et al., Cloning of two carotenoid ketolase genes from *Nostoc punctiforme* for the heterologous production of canthaxanthin and astaxanthin, Biotechnology Letters, vol. 26:813-817, 2004.
Katsuhiro Sakano et al., Degradation of Endogenous Organic Acids Induced by Pi Uptake in *Catharanthus roseus* Cells: Involvement of the Biochemical pH-Stat, Plant Cell Phys., vol. 39(6):615-619, 1998.
Norihiko Misawa et al., Elucidation of the *Erwinia uredovora* Carotenoid Biosynthetic Pathway by Functional Analysis of Gene Products Expressed in *Escherichia coli*, Journal of Bacteriology, vol. 172(12):6704-6712, Dec. 1990.
David W. Leung et al., A Method for Random Mutagenesis of a Defined DNA Segment Using a Modified Polymerase Chain Reaction, Technique-J. Methods in Cell and Mol. Biol., vol. 1(1):11-15, 1989.
Delphine Lagarde et al., The zeaxanthin biosynthesis enzyme beta-carotene hydroxylase is involved in myxoxanthophyll synthesis in *Synechocystis* sp. PCC 6803, Febs Letters, vol. 454:247-251, 1999.
Hartmut Linden, Carotenoid hydroxylase from *Haematococcus pluvialis*: cDNA sequence, regulation and functional complementation, Biochimica et Biophysica Acta, vol. 1446:203-212, 1999.
Georg Schnurr et al., Mapping of a carotenogenic gene cluster from *Erwinia herbicola* and functional identification of six genes, FEMS Microbiology Letters, vol. 78:157-162, 1991.
Norihiko Misawa et al., Structure and Functional Analysis of a Marine Bacterial Carotenoid Biosynthesis Gene Cluster and Astaxanthin Biosynthetic Pathway Proposed at the Gene Level, J. of Bacteriology, vol. 177(22):6575-6584, 1995.

(Continued)

*Primary Examiner*—Tekchand Saidha
*Assistant Examiner*—Christian L. Fronda

(57) ABSTRACT

Protein engineered nucleic acid fragments encoding a CrtO ketolase and a CrtZ hydroxylase are provided with increased astaxanthin synthesis activity. Methods using the present nucleic acid fragments are also provided for increasing or altering astaxanthin production in suitable production hosts.

9 Claims, 1 Drawing Sheet

OTHER PUBLICATIONS

Figure 1:
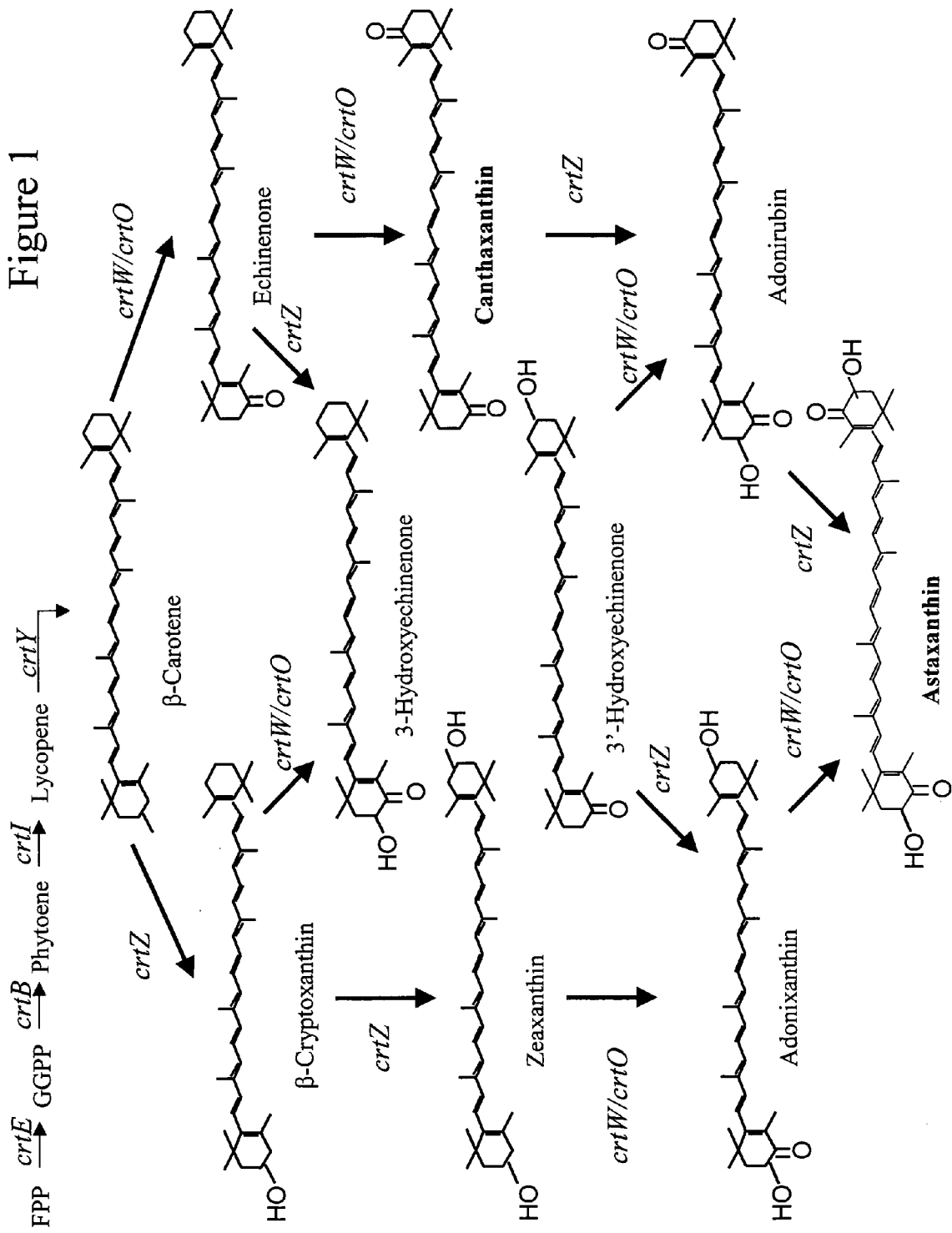

Luis Pasamontes et al., Isolation and characterization of the carotenoid biosynthesis genes of *Flavobacterium* sp. strain R1534, Gene, vol. 185:35-41, 1997.

Bhupinder S. Hundle et al., In vitro expression and activity of lycopene cyclase and beta-carotene hydroxylase from *Erwinia herbicola*, FEBS, vol. 315(3):329-334, 1993.

Li Tian et al., Characterization of a second carotenoid beta-hydroxylase gene from *Arabidopsis* and its relationship to the LUT1 locus, Plant Mol. Biol., vol. 47:379-388, 2001.

Laure Hannibal et al., Isolation and Characterization of Canthaxanthin Biosynthesis Genes from the Photosynthetic Bacterium *Bradyrhizobium* sp. Strain ORS278, J. of Bacteriology, vol. 182(13):3850-3853, 2000.

Zairen Sun et al., Differential expression of two isopentenyl pyrophosphate isomerases and enhanced carotenoid accumulation in a unicellular chlorophyte, PNAS, vol. 95:11482-11488, 1998.

Jurgen Breitenbach et al., Expression in *Escherichia coli* and properties of the carotene ketolase from *Haematococcus pluvialis*, FEMS Microbiology Letters, vol. 140:241-246, 1996.

Delphine Lagarde et al., Increased Production of Zeaxanthin and Other Pigments by Application of Genetic Engineering Techniques to *Synechocystis* sp. Strain PCC 6803, Applied and Environmental Microbiology, vol. 66(1):64-72, 2000.

Mark Harker et al., Biosynthesis of ketocarotenoids in transgenic cyanobacteria expressing the algal gene for beta-C-4-oxygenase, crtO, FEBS Letters, vol. 404:129-134, 1997.

Alexandre Melnikov et al., Random mutagenesis by recombinational capture of PCR products in *Bacillus subtilis* and *Acinetobacter calcoaceticus*, Nucl. Acids Res., vol. 27(4):1056-1062, 1999.

* cited by examiner

SEQUENCE LISTING

```
<160> NUMBER OF SEQ ID NOS: 24

<210> SEQ ID NO 1
<211> LENGTH: 1599
<212> TYPE: DNA
<213> ORGANISM: artificial sequence
<220> FEATURE:
<223> OTHER INFORMATION: Mutant crtO ketolase
<220> FEATURE:
<221> NAME/KEY: CDS
<222> LOCATION: (1)..(1599)

<400> SEQUENCE: 1 atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
            20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
        35                  40                  45
```

```
ttt ccc gga tac aag gtg gac cgg ggg tcg tct gcg cac ctc atg atc        192
Phe Pro Gly Tyr Lys Val Asp Arg Gly Ser Ser Ala His Leu Met Ile
     50              55                  60 cga cac agt ggc atc atc gag gaa ctc gga ctc ggc gcg cac ggc ctt        240
Arg His Ser Gly Ile Ile Glu Glu Leu Gly Leu Gly Ala His Gly Leu
 65              70                  75                  80 cgc tac atc gac tgt gac ccg tgg gcg ttc gct ccg ccc gcc cct ggc        288
Arg Tyr Ile Asp Cys Asp Pro Trp Ala Phe Ala Pro Pro Ala Pro Gly
                     85                  90                  95 acc gac ggg ccg ggc atc gtg ttt cat cgc gac ctc gat gca acc tgc        336
Thr Asp Gly Pro Gly Ile Val Phe His Arg Asp Leu Asp Ala Thr Cys
             100                 105                 110 cag tcc atc gaa cga gct tgc ggg aca aag gac gcc gac gcg tac cgg        384
Gln Ser Ile Glu Arg Ala Cys Gly Thr Lys Asp Ala Asp Ala Tyr Arg
         115                 120                 125 cgg ttc gtc gcg gtc tgg tcg gag cgc agc cga cac gtg ttg aag gca        432
Arg Phe Val Ala Val Trp Ser Glu Arg Ser Arg His Val Leu Lys Ala
 130                 135                 140 ttt tcc aca ccg ccc acc gga tcg aac ctg atc ggt gcg ttc gga gga        480
Phe Ser Thr Pro Pro Thr Gly Ser Asn Leu Ile Gly Ala Phe Gly Gly
145                 150                 155                 160 ctg gcc aca gtg cgc ggc aac agc gaa ctg tcg cgg cag ttc ctc gcg        528
Leu Ala Thr Val Arg Gly Asn Ser Glu Leu Ser Arg Gln Phe Leu Ala
                 165                 170                 175 ccg ggc gac gca ctg ctg gac gag tat ttc gac agt gag gca ctc aag        576
Pro Gly Asp Ala Leu Leu Asp Glu Tyr Phe Asp Ser Glu Ala Leu Lys
             180                 185                 190 gca gcg ttg gcg tgg ttc ggc gcc cag tcc ggg cct ccg atg tcg gaa        624
Ala Ala Leu Ala Trp Phe Gly Ala Gln Ser Gly Pro Pro Met Ser Glu
         195                 200                 205 ccg gga acc gct ccg atg gtc ggc ttc gcg gcc ctc atg cac gtc ctg        672
Pro Gly Thr Ala Pro Met Val Gly Phe Ala Ala Leu Met His Val Leu
 210                 215                 220 ccg ccc ggg cga gca gtc gga ggg agc ggc gca ctg agt gct gcg ttg        720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc        768
Ala Ser Arg Met Ala Val Asp Gly Ala Thr Val Ala Leu Gly Asp Gly
                 245                 250                 255 gtg acg tcg atc cgc cgg aac tcg aat cac tgg acc gtc aca acc gag        816
Val Thr Ser Ile Arg Arg Asn Ser Asn His Trp Thr Val Thr Thr Glu
             260                 265                 270 agc ggt cga gaa gtt cac gct cgc aag gta atc gcg ggt tgc cac atc        864
Ser Gly Arg Glu Val His Ala Arg Lys Val Ile Ala Gly Cys His Ile
         275                 280                 285 ctc acg aca ctc gat ctc ctg ggc aac gga ggc ttc gac cga acc aag        912
Leu Thr Thr Leu Asp Leu Leu Gly Asn Gly Gly Phe Asp Arg Thr Lys
 290                 295                 300 ctc gat cac tgg cgg cgg aag atc agg gtc ggc ccc ggc atc ggc gct        960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc       1008
Val Leu Arg Leu Ala Thr Ser Ala Leu Pro Ser Tyr Arg Gly Asp Ala
                 325                 330                 335 acg aca cgg gaa agt acc tcg gga ttg caa tta ctc gtt tcc gat cgc       1056
Thr Thr Arg Glu Ser Thr Ser Gly Leu Gln Leu Leu Val Ser Asp Arg
             340                 345                 350 gcc cac ttg cgc act gca cac ggc gca gca ctg gca ggg gaa ctg cct       1104
Ala His Leu Arg Thr Ala His Gly Ala Ala Leu Ala Gly Glu Leu Pro
         355                 360                 365
```

```
cct cgc cct gcg gtt ctc gga atg agt ttc agc gga atc gat ccc acg    1152
Pro Arg Pro Ala Val Leu Gly Met Ser Phe Ser Gly Ile Asp Pro Thr
    370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
    450                 455                 460 ctc gat cag atg atg ttg tgg cga ccg ctt ccc gaa ttg tcc ggc cat    1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt    1584
Ala Leu Ser Asp Ser Arg Trp Gly Lys Ala Ser Gln Trp Met Arg Arg
        515                 520                 525 tcg agc cgc tcg tga                                                1599
Ser Ser Arg Ser
    530

<210> SEQ ID NO 2
<211> LENGTH: 532
<212> TYPE: PRT
<213> ORGANISM: artificial sequence
<220> FEATURE:
<223> OTHER INFORMATION: Synthetic Construct

<400> SEQUENCE: 2

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125
```

-continued

```
Arg Phe Val Ala Val Trp Ser Glu Arg Ser Arg His Val Leu Lys Ala
130                 135                 140
Phe Ser Thr Pro Pro Thr Gly Ser Asn Leu Ile Gly Ala Phe Gly Gly
145                 150                 155                 160
Leu Ala Thr Val Arg Gly Asn Ser Glu Leu Ser Arg Gln Phe Leu Ala
                165                 170                 175
Pro Gly Asp Ala Leu Leu Asp Glu Tyr Phe Asp Ser Glu Ala Leu Lys
            180                 185                 190
Ala Ala Leu Ala Trp Phe Gly Ala Gln Ser Gly Pro Pro Met Ser Glu
        195                 200                 205
Pro Gly Thr Ala Pro Met Val Gly Phe Ala Ala Leu Met His Val Leu
    210                 215                 220
Pro Pro Gly Arg Ala Val Gly Gly Ser Gly Ala Leu Ser Ala Ala Leu
225                 230                 235                 240
Ala Ser Arg Met Ala Val Asp Gly Ala Thr Val Ala Leu Gly Asp Gly
                245                 250                 255
Val Thr Ser Ile Arg Arg Asn Ser Asn His Trp Thr Val Thr Thr Glu
            260                 265                 270
Ser Gly Arg Glu Val His Ala Arg Lys Val Ile Ala Gly Cys His Ile
        275                 280                 285
Leu Thr Thr Leu Asp Leu Leu Gly Asn Gly Gly Phe Asp Arg Thr Lys
    290                 295                 300
Leu Asp His Trp Arg Arg Lys Ile Arg Val Gly Pro Gly Ile Gly Ala
305                 310                 315                 320
Val Leu Arg Leu Ala Thr Ser Ala Leu Pro Ser Tyr Arg Gly Asp Ala
                325                 330                 335
Thr Thr Arg Glu Ser Thr Ser Gly Leu Gln Leu Leu Val Ser Asp Arg
            340                 345                 350
Ala His Leu Arg Thr Ala His Gly Ala Ala Leu Ala Gly Glu Leu Pro
        355                 360                 365
Pro Arg Pro Ala Val Leu Gly Met Ser Phe Ser Gly Ile Asp Pro Thr
    370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
            420                 425                 430
Thr Asp Ser Val Leu Asp Arg Phe Ile Gln Thr Pro Arg Asp Ile Glu
        435                 440                 445
Ser Glu Leu Gly Met Ile Gly Asn Val Met His Val Glu Met Ser
    450                 455                 460
Leu Asp Gln Met Met Leu Trp Arg Pro Leu Pro Glu Leu Ser Gly His
465                 470                 475                 480
Arg Val Pro Gly Ala Asp Gly Leu Tyr Leu Thr Gly Ala Ser Thr His
                485                 490                 495
Pro Gly Gly Gly Val Ser Gly Ala Ser Gly Arg Ser Ala Ala Arg Ile
            500                 505                 510
Ala Leu Ser Asp Ser Arg Trp Gly Lys Ala Ser Gln Trp Met Arg Arg
        515                 520                 525
Ser Ser Arg Ser
530
```

```
<210> SEQ ID NO 3
<211> LENGTH: 30
<212> TYPE: DNA
<213> ORGANISM: artificial sequence
<220> FEATURE:
<223> OTHER INFORMATION: Primer

<400> SEQUENCE: 3
actagtaagg aggaataaac catgagcgca                                          30

<210> SEQ ID NO 4
<211> LENGTH: 36
<212> TYPE: DNA
<213> ORGANISM: artificial sequence
<220> FEATURE:
<223> OTHER INFORMATION: Primer

<400> SEQUENCE: 4
tgtacagcta gctcacgagc ggctcgaacg acgcat                                   36

<210> SEQ ID NO 5
<211> LENGTH: 486
<212> TYPE: DNA
<213> ORGANISM: Brevundimonas vesicularis DC263
<220> FEATURE:
<221> NAME/KEY: CDS
<222> LOCATION: (1)..(486)

<400> SEQUENCE: 5 atg tcc tgg ccg acg atg atc ctg ctg ttc ctc gcc acc ttc ctg ggg           48
Met Ser Trp Pro Thr Met Ile Leu Leu Phe Leu Ala Thr Phe Leu Gly
1               5                   10                  15 atg gag gtc ttc gcc tgg gcg atg cat cgc tat gtc atg cac ggc ctg           96
Met Glu Val Phe Ala Trp Ala Met His Arg Tyr Val Met His Gly Leu
                20                  25                  30 ctg tgg acc tgg cac cgc agc cat cat gag ccg cac gac gac gtg ctg          144
Leu Trp Thr Trp His Arg Ser His His Glu Pro His Asp Asp Val Leu
            35                  40                  45 gaa agg aac gac ctg ttc gcg gtg gtg ttc gcc gcc ccg gcc atc atc          192
Glu Arg Asn Asp Leu Phe Ala Val Val Phe Ala Ala Pro Ala Ile Ile
        50                  55                  60 ctc gtc gcc ttg ggt cta cat ctg tgg cct tgg atg ctg ccg atc ggc          240
Leu Val Ala Leu Gly Leu His Leu Trp Pro Trp Met Leu Pro Ile Gly
65                  70                  75                  80 ctg ggc gtt acg gcc tat gga ctg gtt tat ttc ttc ttt cac gac ggg          288
Leu Gly Val Thr Ala Tyr Gly Leu Val Tyr Phe Phe Phe His Asp Gly
                85                  90                  95 ctg gtg cat cgc cgg ttc ccg aca ggg atc gca ggg cgc tcg gcg ttc          336
Leu Val His Arg Arg Phe Pro Thr Gly Ile Ala Gly Arg Ser Ala Phe
                100                 105                 110 tgg acg cga cgc att cag gcc cac cgg ctg cat cac gcg gtg cgg aca          384
Trp Thr Arg Arg Ile Gln Ala His Arg Leu His His Ala Val Arg Thr
            115                 120                 125 cgc gag ggc tgc gta tcg ttc ggc ttc ctt tgg gtg cgg tcg gcg cgc          432
Arg Glu Gly Cys Val Ser Phe Gly Phe Leu Trp Val Arg Ser Ala Arg
        130                 135                 140 gcg ctg aag gcc gaa ctg tct cag aaa cgc ggc tca tcc agc aac ggc          480
Ala Leu Lys Ala Glu Leu Ser Gln Lys Arg Gly Ser Ser Ser Asn Gly
145                 150                 155                 160 gcc tga                                                                  486
Ala

<210> SEQ ID NO 6
```

```
<211> LENGTH: 161
<212> TYPE: PRT
<213> ORGANISM: Brevundimonas vesicularis DC263

<400> SEQUENCE: 6

Met Ser Trp Pro Thr Met Ile Leu Leu Phe Leu Ala Thr Phe Leu Gly
1               5                   10                  15

Met Glu Val Phe Ala Trp Ala Met His Arg Tyr Val Met His Gly Leu
            20                  25                  30

Leu Trp Thr Trp His Arg Ser His Glu Pro His Asp Asp Val Leu
        35                  40                  45

Glu Arg Asn Asp Leu Phe Ala Val Val Phe Ala Ala Pro Ala Ile Ile
    50                  55                  60

Leu Val Ala Leu Gly Leu His Leu Trp Pro Trp Met Leu Pro Ile Gly
65                  70                  75                  80

Leu Gly Val Thr Ala Tyr Gly Leu Val Tyr Phe Phe Phe His Asp Gly
                85                  90                  95

Leu Val His Arg Arg Phe Pro Thr Gly Ile Ala Gly Arg Ser Ala Phe
            100                 105                 110

Trp Thr Arg Arg Ile Gln Ala His Arg Leu His His Ala Val Arg Thr
        115                 120                 125

Arg Glu Gly Cys Val Ser Phe Gly Phe Leu Trp Val Arg Ser Ala Arg
    130                 135                 140

Ala Leu Lys Ala Glu Leu Ser Gln Lys Arg Gly Ser Ser Ser Asn Gly
145                 150                 155                 160

Ala

<210> SEQ ID NO 7
<211> LENGTH: 42
<212> TYPE: DNA
<213> ORGANISM: artificial sequence
<220> FEATURE:
<223> OTHER INFORMATION: Primer

<400> SEQUENCE: 7
tctagaaagg aggaataaac catgtcctgg ccgacgatga tc                          42

<210> SEQ ID NO 8
<211> LENGTH: 26
<212> TYPE: DNA
<213> ORGANISM: artificial sequence
<220> FEATURE:
<223> OTHER INFORMATION: Primer

<400> SEQUENCE: 8
actagtcagg cgccgttgct ggatga                                            26

<210> SEQ ID NO 9
<211> LENGTH: 534
<212> TYPE: DNA
<213> ORGANISM: Enterobacteriaceae DC260
<220> FEATURE:
<221> NAME/KEY: CDS
<222> LOCATION: (1)..(534)

<400> SEQUENCE: 9 atg ctc tgg tta tgg aac gtg ctt atc ttg ttg gca acc gtg gtg gtg       48
Met Leu Trp Leu Trp Asn Val Leu Ile Leu Leu Ala Thr Val Val Val
1               5                   10                  15 atg gaa atc gta gcg gcg ctg tcg cat aaa tac atc atg cac ggt tgg       96
Met Glu Ile Val Ala Ala Leu Ser His Lys Tyr Ile Met His Gly Trp
```

-continued

```
            20                  25                  30
gga tgg ggc tgg cat ctg tcg cac cat gaa ccg cac agc ggt aag ttt     144
Gly Trp Gly Trp His Leu Ser His His Glu Pro His Ser Gly Lys Phe
         35                  40                  45 gag ctc aac gat ctt tat gcg gtg gtg ttt gcg gta ctg gcg att gtg     192
Glu Leu Asn Asp Leu Tyr Ala Val Val Phe Ala Val Leu Ala Ile Val
 50                  55                  60 ctg att tat gtc ggt gtg caa ggc atg tgg ccg ctg cag tgg att ggt     240
Leu Ile Tyr Val Gly Val Gln Gly Met Trp Pro Leu Gln Trp Ile Gly
 65                  70                  75                  80 gcc gga atg acg acg tac ggc gcg ctc tac ttc atg gtg cac gat ggc     288
Ala Gly Met Thr Thr Tyr Gly Ala Leu Tyr Phe Met Val His Asp Gly
                 85                  90                  95 ctg gtg cat caa cgc tgg ccg ttc cgc tat atc ccg cgc aaa ggc tat     336
Leu Val His Gln Arg Trp Pro Phe Arg Tyr Ile Pro Arg Lys Gly Tyr
            100                 105                 110 ctt aag cgc tta tac atg gcg cac cgc atg cat cat gcg gtg cgc ggg     384
Leu Lys Arg Leu Tyr Met Ala His Arg Met His His Ala Val Arg Gly
        115                 120                 125 cgt gaa ggc tgc gtg tcg ttt ggt ttc ctc tac gcg cca ccg ctg aat     432
Arg Glu Gly Cys Val Ser Phe Gly Phe Leu Tyr Ala Pro Pro Leu Asn
    130                 135                 140 aag ctg caa gcc acg ctg cgc cag cgt cac gga cgt aaa atc aac gag     480
Lys Leu Gln Ala Thr Leu Arg Gln Arg His Gly Arg Lys Ile Asn Glu
145                 150                 155                 160 gac gct gcc aca gac cag ccg gac gcg gtt cag gac gag aca cac gcg     528
Asp Ala Ala Thr Asp Gln Pro Asp Ala Val Gln Asp Glu Thr His Ala
                165                 170                 175 aag tga                                                             534
Lys
```

<210> SEQ ID NO 10
<211> LENGTH: 177
<212> TYPE: PRT
<213> ORGANISM: Enterobacteriaceae DC260

<400> SEQUENCE: 10

```
Met Leu Trp Leu Trp Asn Val Leu Ile Leu Leu Ala Thr Val Val Val
 1               5                  10                  15

Met Glu Ile Val Ala Ala Leu Ser His Lys Tyr Ile Met His Gly Trp
                20                  25                  30

Gly Trp Gly Trp His Leu Ser His His Glu Pro His Ser Gly Lys Phe
         35                  40                  45

Glu Leu Asn Asp Leu Tyr Ala Val Val Phe Ala Val Leu Ala Ile Val
 50                  55                  60

Leu Ile Tyr Val Gly Val Gln Gly Met Trp Pro Leu Gln Trp Ile Gly
 65                  70                  75                  80

Ala Gly Met Thr Thr Tyr Gly Ala Leu Tyr Phe Met Val His Asp Gly
                 85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Arg Glu Gly Cys Val Ser Phe Gly Phe Leu Tyr Ala Pro Pro Leu Asn
    130                 135                 140

Lys Leu Gln Ala Thr Leu Arg Gln Arg His Gly Arg Lys Ile Asn Glu
145                 150                 155                 160
```

Asp Ala Ala Thr Asp Gln Pro Asp Ala Val Gln Asp Glu Thr His Ala
            165                 170                 175
Lys

<210> SEQ ID NO 11
<211> LENGTH: 43
<212> TYPE: DNA
<213> ORGANISM: artificial sequence
<220> FEATURE:
<223> OTHER INFORMATION: Primer

<400> SEQUENCE: 11
actagtaagg aggaataaac catgctctgg ttatggaacg tgc                43

<210> SEQ ID NO 12
<211> LENGTH: 27
<212> TYPE: DNA
<213> ORGANISM: artificial sequence
<220> FEATURE:
<223> OTHER INFORMATION: Primer

<400> SEQUENCE: 12
actagttcac ttcgcgtgtg tctcgtc                                  27

<210> SEQ ID NO 13
<211> LENGTH: 23
<212> TYPE: DNA
<213> ORGANISM: artificial sequence
<220> FEATURE:
<223> OTHER INFORMATION: Primer

<400> SEQUENCE: 13
gcagcgtgca gctcatgcag ttc                                      23

<210> SEQ ID NO 14
<211> LENGTH: 24
<212> TYPE: DNA
<213> ORGANISM: artificial sequence
<220> FEATURE:
<223> OTHER INFORMATION: Primer

<400> SEQUENCE: 14
ccagaccgtt cagctggata ttac                                     24

<210> SEQ ID NO 15
<211> LENGTH: 2106
<212> TYPE: DNA
<213> ORGANISM: artificial sequence
<220> FEATURE:
<223> OTHER INFORMATION: Nucleic acid fragment encoding mutant crtOZ
      gene pair from strain 356M4003.

<400> SEQUENCE: 15
atgagcgcat ttctcgacgc cgtcgtcgtc ggttccggac acaacgctct cgtttcggcc    60
gcgtatctcg cccgtgaggg ttggtcggtc gaggttctcg agaaggacac ggttctcggc   120
ggtgccgtct cgaccgtcga gcgatttccc ggatacaagg tggaccgggg gtcgtctgcg   180
cacctcatga tccgacacag tggcatcatc gaggaactcg gactcggcgc gcacggcctt   240
cgctacatcg actgtgaccc gtgggcgttc gctccgcccg ccctggcac cgacgggccg   300 ggcatcgtgt tcatcgcga cctcgatgca acctgccagt ccatcgaacg agcttgcggg   360
acaaaggacg ccgacgcgta ccggcggttc gtcgcggtct ggtcgagcg cagccgacac   420 gtgttgaagg catttccac accgcccacc ggatcgaacc tgatcggtgc gttcggagga   480

-continued

```
ctggccacag tgcgcggcaa cagcgaactg tcgcggcagt tcctcgcgcc gggcgacgca      540
ctgctggacg agtatttcga cagtgaggca ctcaaggcag cgttggcgtg gttcggcgcc      600
cagtccggac ctccgatgtc ggaaccggga accgctccga tggtcggctt cgcggccctc      660
atgcacgtcc tgccgcccgg gcgagcagtc ggagggagcg gcgcactgag tgctgcgttg      720
gcatcccgga tggctgtcga cggcgccacc gtcgcgctcg gtgacggcgt gacgtcgatc      780
cgccggaact cgaatcactg gaccgtcaca accgagagcg gtcgagaagt tcacgctcgc      840
aaggtaatcg cgggttgcca catcctcacg acactcgatc tcctgggcaa cggaggcttc      900
gaccgaacca agcttgatca ctggcggcgg aagatcaggg tcggcccgg catcggcgct       960 gtattgcgac tggcgacatc tgcgctcccg tcctaccgcg cgacgccac gacacgggaa      1020 agtacctcgg gattgcaatt actcgtttcc gatcgcgccc acttgcgcac tgcacacggc     1080
gcagcactgg caggggaact gcctcctcgc cctgcggttc tcggaatgag tttcagcgga     1140
atcgatccca cgatcgcccc ggccgggcgg catcaggtga cactgtggtc gcagtggcag     1200
ccgtatcgtc tcagcggaca tcgcgattgg gcgtcggtcg ccgaggccga ggccgaccgg     1260
atcgtcggcg agatggaggc ttttgcaccc ggattcaccg attccgtcct cgaccgcttc     1320
attcaaactc cccgcgacat cgagtcggaa ttggggatga tcggcggaaa tgtcatgcac     1380
gtcgagatgt cactcgatca gatgatgttg tggcgaccgc ttcccgaatt gtccggccat     1440
cgcgttccgg gagcagacgg gttgtatctg accggagcct cgacgcatcc cggtggtggt     1500
gtgtccggag ccagtggtcg cagtgccgct cgaatcgcac tgtccgacag ccgctggggt     1560
aaagcgagtc agtggatgcg tcgttcgagc cgctcgtgag ctagaaagga ggaataaacc     1620
atgtcctggc cgacgatgat cctgctgttc ctcgccacct tcctggggat ggaggtcttc     1680
gcctgggcga tgcatcgcta tgtcatgcac ggcctgctgt ggacctggca ccgcagccat     1740
catgagccgc acgacgacgt gctggaaagg aacgacccgt tcgcggtggt gttcgccgcc     1800
ccggccatca tcctcgtcgc cttgggtcta catctgtggc cttggatgct gccgatcggc     1860
ctgggcgtta ctgcctatgg actggtttat ttcttctttc acgacgggct ggtgcatcgc     1920
cggttcccga cagggatcgc agggcgctcg gcgttctgga cgcgacgcat tcaggcccac     1980
cggctgcatc acgcggtgcg gacccgcgag ggctgcgtat cgttcggctt cctttgggtg     2040
cggtcggcgc gcgcgctgaa ggccgaactg tctcagaaac gcggctcatc cagcaacggc     2100
gcctga                                                                2106
```

<210> SEQ ID NO 16
<211> LENGTH: 1599
<212> TYPE: DNA
<213> ORGANISM: artificial sequence
<220> FEATURE:
<223> OTHER INFORMATION: Mutant crtO coding sequence from strain
      356M4003
<220> FEATURE:
<221> NAME/KEY: CDS
<222> LOCATION: (1)..(1599)

<400> SEQUENCE: 16

```
atg agc gca ttt ctc gac gcc gtc gtc gtc ggt tcc gga cac aac gct      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
            20                  25                  30
```

-continued

| | | |
|---|---|---|
| ctc gag aag gac acg gtt ctc ggc ggt gcc gtc tcg acc gtc gag cga<br>Leu Glu Lys Asp Thr Val Leu Gly Gly Ala Val Ser Thr Val Glu Arg<br>35 40 45 | | 144 |
| ttt ccc gga tac aag gtg gac cgg ggg tcg tct gcg cac ctc atg atc<br>Phe Pro Gly Tyr Lys Val Asp Arg Gly Ser Ser Ala His Leu Met Ile<br>50 55 60 | | 192 |
| cga cac agt ggc atc atc gag gaa ctc gga ctc ggc gcg cac ggc ctt<br>Arg His Ser Gly Ile Ile Glu Glu Leu Gly Leu Gly Ala His Gly Leu<br>65 70 75 80 | | 240 |
| cgc tac atc gac tgt gac ccg tgg gcg ttc gct ccg ccc gcc cct ggc<br>Arg Tyr Ile Asp Cys Asp Pro Trp Ala Phe Ala Pro Pro Ala Pro Gly<br>85 90 95 | | 288 |
| acc gac ggg ccg ggc atc gtg ttt cat cgc gac ctc gat gca acc tgc<br>Thr Asp Gly Pro Gly Ile Val Phe His Arg Asp Leu Asp Ala Thr Cys<br>100 105 110 | | 336 |
| cag tcc atc gaa cga gct tgc ggg aca aag gac gcc gac gcg tac cgg<br>Gln Ser Ile Glu Arg Ala Cys Gly Thr Lys Asp Ala Asp Ala Tyr Arg<br>115 120 125 | | 384 |
| cgg ttc gtc gcg gtc tgg tcg gag cgc agc cga cac gtg ttg aag gca<br>Arg Phe Val Ala Val Trp Ser Glu Arg Ser Arg His Val Leu Lys Ala<br>130 135 140 | | 432 |
| ttt tcc aca ccg ccc acc gga tcg aac ctg atc ggt gcg ttc gga gga<br>Phe Ser Thr Pro Pro Thr Gly Ser Asn Leu Ile Gly Ala Phe Gly Gly<br>145 150 155 160 | | 480 |
| ctg gcc aca gtg cgc ggc aac agc gaa ctg tcg cgg cag ttc ctc gcg<br>Leu Ala Thr Val Arg Gly Asn Ser Glu Leu Ser Arg Gln Phe Leu Ala<br>165 170 175 | | 528 |
| ccg ggc gac gca ctg ctg gac gag tat ttc gac agt gag gca ctc aag<br>Pro Gly Asp Ala Leu Leu Asp Glu Tyr Phe Asp Ser Glu Ala Leu Lys<br>180 185 190 | | 576 |
| gca gcg ttg gcg tgg ttc ggc gcc cag tcc gga cct ccg atg tcg gaa<br>Ala Ala Leu Ala Trp Phe Gly Ala Gln Ser Gly Pro Pro Met Ser Glu<br>195 200 205 | | 624 |
| ccg gga acc gct ccg atg gtc ggc ttc gcg gcc ctc atg cac gtc ctg<br>Pro Gly Thr Ala Pro Met Val Gly Phe Ala Ala Leu Met His Val Leu<br>210 215 220 | | 672 |
| ccg ccc ggg cga gca gtc gga ggg agc ggc gca ctg agt gct gcg ttg<br>Pro Pro Gly Arg Ala Val Gly Gly Ser Gly Ala Leu Ser Ala Ala Leu<br>225 230 235 240 | | 720 |
| gca tcc cgg atg gct gtc gac ggc gcc acc gtc gcg ctc ggt gac ggc<br>Ala Ser Arg Met Ala Val Asp Gly Ala Thr Val Ala Leu Gly Asp Gly<br>245 250 255 | | 768 |
| gtg acg tcg atc cgc cgg aac tcg aat cac tgg acc gtc aca acc gag<br>Val Thr Ser Ile Arg Arg Asn Ser Asn His Trp Thr Val Thr Thr Glu<br>260 265 270 | | 816 |
| agc ggt cga gaa gtt cac gct cgc aag gta atc gcg ggt tgc cac atc<br>Ser Gly Arg Glu Val His Ala Arg Lys Val Ile Ala Gly Cys His Ile<br>275 280 285 | | 864 |
| ctc acg aca ctc gat ctc ctg ggc aac gga ggc ttc gac cga acc aag<br>Leu Thr Thr Leu Asp Leu Leu Gly Asn Gly Gly Phe Asp Arg Thr Lys<br>290 295 300 | | 912 |
| ctt gat cac tgg cgg cgg aag atc agg gtc ggc ccc ggc atc ggc gct<br>Leu Asp His Trp Arg Arg Lys Ile Arg Val Gly Pro Gly Ile Gly Ala<br>305 310 315 320 | | 960 |
| gta ttg cga ctg gcg aca tct gcg ctc ccg tcc tac cgc ggc gac gcc<br>Val Leu Arg Leu Ala Thr Ser Ala Leu Pro Ser Tyr Arg Gly Asp Ala<br>325 330 335 | | 1008 |
| acg aca cgg gaa agt acc tcg gga ttg caa tta ctc gtt tcc gat cgc<br>Thr Thr Arg Glu Ser Thr Ser Gly Leu Gln Leu Leu Val Ser Asp Arg<br>340 345 350 | | 1056 |

```
gcc cac ttg cgc act gca cac ggc gca gca ctg gca ggg gaa ctg cct      1104
Ala His Leu Arg Thr Ala His Gly Ala Ala Leu Ala Gly Glu Leu Pro
        355                 360                 365 cct cgc cct gcg gtt ctc gga atg agt ttc agc gga atc gat ccc acg      1152
Pro Arg Pro Ala Val Leu Gly Met Ser Phe Ser Gly Ile Asp Pro Thr
370                 375                 380 atc gcc ccg gcc ggg cgg cat cag gtg aca ctg tgg tcg cag tgg cag      1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc      1248
Pro Tyr Arg Leu Ser Gly His Arg Asp Trp Ala Ser Val Ala Glu Ala
                405                 410                 415 gag gcc gac cgg atc gtc ggc gag atg gag gct ttt gca ccc gga ttc      1296
Glu Ala Asp Arg Ile Val Gly Glu Met Glu Ala Phe Ala Pro Gly Phe
            420                 425                 430 acc gat tcc gtc ctc gac cgc ttc att caa act ccc cgc gac atc gag      1344
Thr Asp Ser Val Leu Asp Arg Phe Ile Gln Thr Pro Arg Asp Ile Glu
        435                 440                 445 tcg gaa ttg ggg atg atc ggc gga aat gtc atg cac gtc gag atg tca      1392
Ser Glu Leu Gly Met Ile Gly Gly Asn Val Met His Val Glu Met Ser
450                 455                 460 ctc gat cag atg atg ttg tgg cga ccg ctt ccc gaa ttg tcc ggc cat      1440
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat      1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc      1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt      1584
Ala Leu Ser Asp Ser Arg Trp Gly Lys Ala Ser Gln Trp Met Arg Arg
        515                 520                 525 tcg agc cgc tcg tga                                                   1599
Ser Ser Arg Ser
    530

<210> SEQ ID NO 17
<211> LENGTH: 532
<212> TYPE: PRT
<213> ORGANISM: artificial sequence
<220> FEATURE:
<223> OTHER INFORMATION: Synthetic Construct

<400> SEQUENCE: 17

Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110
```

-continued

```
Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Lys
    290                 295                 300

Leu Asp His Trp Arg Arg Lys Ile Arg Val Gly Pro Gly Ile Gly Ala
305                 310                 315                 320

Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
            340                 345                 350

Ala His Leu Arg Thr Ala His Gly Ala Ala Leu Ala Gly Glu Leu Pro
        355                 360                 365

Pro Arg Pro Ala Val Leu Gly Met Ser Phe Ser Gly Ile Asp Pro Thr
    370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
            420                 425                 430

Thr Asp Ser Val Leu Asp Arg Phe Ile Gln Thr Pro Arg Asp Ile Glu
        435                 440                 445

Ser Glu Leu Gly Met Ile Gly Gly Asn Val Met His Val Glu Met Ser
    450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
            500                 505                 510

Ala Leu Ser Asp Ser Arg Trp Gly Lys Ala Ser Gln Trp Met Arg Arg
        515                 520                 525
```

```
-continued

Ser Ser Arg Ser
    530

<210> SEQ ID NO 18
<211> LENGTH: 486
<212> TYPE: DNA
<213> ORGANISM: artificial sequence
<220> FEATURE:
<223> OTHER INFORMATION: Mutant crtZ coding sequence from strain
      356M4003
<220> FEATURE:
<221> NAME/KEY: CDS
<222> LOCATION: (1)..(486)

<400> SEQUENCE: 18 atg tcc tgg ccg acg atg atc ctg ctg ttc ctc gcc acc ttc ctg ggg      48
Met Ser Trp Pro Thr Met Ile Leu Leu Phe Leu Ala Thr Phe Leu Gly
 1               5                  10                  15 atg gag gtc ttc gcc tgg gcg atg cat cgc tat gtc atg cac ggc ctg      96
Met Glu Val Phe Ala Trp Ala Met His Arg Tyr Val Met His Gly Leu
             20                  25                  30 ctg tgg acc tgg cac cgc agc cat cat gag ccg cac gac gac gtg ctg     144
Leu Trp Thr Trp His Arg Ser His His Glu Pro His Asp Asp Val Leu
         35                  40                  45 gaa agg aac gac ccg ttc gcg gtg gtg ttc gcc gcc ccg gcc atc atc     192
Glu Arg Asn Asp Pro Phe Ala Val Val Phe Ala Ala Pro Ala Ile Ile
     50                  55                  60 ctc gtc gcc ttg ggt cta cat ctg tgg cct tgg atg ctg ccg atc ggc     240
Leu Val Ala Leu Gly Leu His Leu Trp Pro Trp Met Leu Pro Ile Gly
 65                  70                  75                  80 ctg ggc gtt act gcc tat gga ctg gtt tat ttc ttt cac gac ggg         288
Leu Gly Val Thr Ala Tyr Gly Leu Val Tyr Phe Phe Phe His Asp Gly
                 85                  90                  95 ctg gtg cat cgc cgg ttc ccg aca ggg atc gca ggg cgc tcg gcg ttc     336
Leu Val His Arg Arg Phe Pro Thr Gly Ile Ala Gly Arg Ser Ala Phe
            100                 105                 110 tgg acg cga cgc att cag gcc cac cgg ctg cat cac gcg gtg cgg acc     384
Trp Thr Arg Arg Ile Gln Ala His Arg Leu His His Ala Val Arg Thr
        115                 120                 125 cgc gag ggc tgc gta tcg ttc ggc ttc ctt tgg gtg cgg tcg gcg cgc     432
Arg Glu Gly Cys Val Ser Phe Gly Phe Leu Trp Val Arg Ser Ala Arg
    130                 135                 140 gcg ctg aag gcc gaa ctg tct cag aaa cgc ggc tca tcc agc aac ggc     480
Ala Leu Lys Ala Glu Leu Ser Gln Lys Arg Gly Ser Ser Ser Asn Gly
145                 150                 155                 160 gcc tga                                                             486
Ala

<210> SEQ ID NO 19
<211> LENGTH: 161
<212> TYPE: PRT
<213> ORGANISM: artificial sequence
<220> FEATURE:
<223> OTHER INFORMATION: Synthetic Construct

<400> SEQUENCE: 19

Met Ser Trp Pro Thr Met Ile Leu Leu Phe Leu Ala Thr Phe Leu Gly
 1               5                  10                  15

Met Glu Val Phe Ala Trp Ala Met His Arg Tyr Val Met His Gly Leu
             20                  25                  30

Leu Trp Thr Trp His Arg Ser His His Glu Pro His Asp Asp Val Leu
         35                  40                  45
```

```
Glu Arg Asn Asp Pro Phe Ala Val Val Phe Ala Ala Pro Ala Ile Ile
 50                  55                  60

Leu Val Ala Leu Gly Leu His Leu Trp Pro Trp Met Leu Pro Ile Gly
 65                  70                  75                  80

Leu Gly Val Thr Ala Tyr Gly Leu Val Tyr Phe Phe His Asp Gly
                 85                  90                  95

Leu Val His Arg Arg Phe Pro Thr Gly Ile Ala Gly Arg Ser Ala Phe
            100                 105                 110

Trp Thr Arg Arg Ile Gln Ala His Arg Leu His His Ala Val Arg Thr
        115                 120                 125

Arg Glu Gly Cys Val Ser Phe Gly Phe Leu Trp Val Arg Ser Ala Arg
130                 135                 140

Ala Leu Lys Ala Glu Leu Ser Gln Lys Arg Gly Ser Ser Ser Asn Gly
145                 150                 155                 160

Ala
```

<210> SEQ ID NO 20
<211> LENGTH: 2106
<212> TYPE: DNA
<213> ORGANISM: artificial sequence
<220> FEATURE:
<223> OTHER INFORMATION: Nucleic acid fragment encoding mutant crtOZ
      gene pair from strain 356M4005.

<400> SEQUENCE: 20

```
atgagcgcat tctcgacgc cgtcgtcgtc ggttccggac acaacgcact cgtttcggcc     60
gcgtatctcg cccgtgaggg ttggtcggtc gaggttctcg agaaggacac ggttctcggc    120
ggtgccgtct cgaccgtcga gcgatttccc ggatacaagg tggaccgggg gtcgtctgcg    180
cacctcatga tccgacacag tggcatcatc gaggaactcg gactcggcgc gcacggcctt    240
cgctacatcg actgtgaccc gtgggcgttc gctccgcccg ccctggcac cgacgggccg     300
ggcatcgtgt tcatcgcga cctcgatgca acctgccagt ccatcgaacg agcttgcggg    360
acaaaggacg ccgacgcgta ccggcggttc gtcgcggtct ggtcggagcg cagccgacac    420
gtgttgaagg cattttccac accgcccacc ggatcgaacc tgatcggtgc gttcggagga    480
ctggccacag tgcgcggcaa cagcgaactg tcgcggcagt cctcgcgcc gggcgacgca    540
ctgctggacg agtatttcga cagtgaggta ctcaaggcag cgttggcgtg gttcggcgcc    600
cagtccgggc ctccgatgtc ggaaccggga accgctccga tggtcggctt cgcggcctc    660
atgcacgtcc tgccgcccgg gcgagcagtc ggagggagcg gcgcactgag tgctgcgttg    720
gcatcccgga tggctgtcga cggcgccacc gtcgcgctcg gtgacggcgt gacgtcgatc    780
cgccggaact cgaatcactg gaccgtcaca accgagagcg gtcgagaagt ccacgctcgc    840
aaggtaatcg cgggttgcca catcctcacg acactcgatc tcctgggcaa cggaggcttc    900
gaccgaacca agcttgatca ctggcggcgg aagatcaggg tcggccccgg catcggcgct    960
gtattgcgac tggcgacatc tgcgctcccg tcctaccgcg gcgacgccac gacacgggaa   1020
agtacctcgg gattgcaatt actcgtttcc gatcgcgccc acttgcgcac tgcacacggc   1080
gcagcactgg cagggaact gcctcctcgc cctgcggttc tcggaatgag tttcagcgga   1140
atcgatccca cgatcgcccc ggccgggcgg catcaggtga cactgtggtc gcagtggcag   1200
ccgtatcgtc tcagcggaca tcgcgattgg gcgtcggtcg ccgaggccga ggccgaccgg   1260
atcgtcggcg agatggaggc ttttgcaccc ggattcaccg attccgtcct cgaccgcttc   1320
attcaaactc ccgcgacat cgagtcggaa ttggggatga tcggcggaaa tgtcatgcac   1380
```

```
gtcgagatgt cactcgatca gatgatgttg tggcgaccgc ttcccgaatt gtccggccat    1440
cgcgttccgg gagcagacgg gttgtatctg accggagcct cgacgcatcc cggtggtggt    1500
gtgtccggag ccagtggtcg cagtgccgct cgaatcgcac tgtccgacag ccgctggggt    1560
aaagcgagtc agtggatgcg tcgttcgagc cgctcgtgag ctagaaagga ggaataaacc    1620
atgtcctggc cgacgatgat cctgctgttc ctcgccacct tcctggggat ggaggtcttc    1680
gcctgggcga tgcatcgcta tgtcatgcac ggcctgctgt ggacctggca ccgcagccat    1740
catgagccgc acgacgacgt gctggaaagg aacgacctgt tcgcggtggt gttcgccgcc    1800
ccggccatca tcctcgtcgc cttgggtcta catctgtggc cttggatgct gccgatcggc    1860
ctgggcgtta cggcctatgg actggtttat tccttctttc acgacgggct ggtgcatcgc    1920
cggttcccga cagggatcgc agggcgctcg gcgttctgga cgcgacgcat tcaggcccac    1980
cggctgcatc acgcggtgcg gacacgcgag ggctgcgtat cgttcggctt cctttggggg    2040
cggtcggcgc gcgcgctgaa ggccgaactg tctcagaaac gcggctcatc cagcaacggc    2100
gcctga                                                              2106
```

```
<210> SEQ ID NO 21
<211> LENGTH: 1599
<212> TYPE: DNA
<213> ORGANISM: artificial sequence
<220> FEATURE:
<223> OTHER INFORMATION: Mutant crtO coding sequence from strain
      356M4005
<220> FEATURE:
<221> NAME/KEY: CDS
<222> LOCATION: (1)..(1599)

<400> SEQUENCE: 21 atg agc gca ttt ctc gac gcc gtc gtc gtc ggt tcc gga cac aac gca      48
Met Ser Ala Phe Leu Asp Ala Val Val Val Gly Ser Gly His Asn Ala
1               5                   10                  15 ctc gtt tcg gcc gcg tat ctc gcc cgt gag ggt tgg tcg gtc gag gtt      96
Leu Val Ser Ala Ala Tyr Leu Ala Arg Glu Gly Trp Ser Val Glu Val
            20                  25                  30 ctc gag aag gac acg gtt ctc ggc ggt gcc gtc tcg acc gtc gag cga     144
Leu Glu Lys Asp Thr Val Leu Gly Gly Ala Val Ser Thr Val Glu Arg
        35                  40                  45 ttt ccc gga tac aag gtg gac cgg ggg tcg tct gcg cac ctc atg atc     192
Phe Pro Gly Tyr Lys Val Asp Arg Gly Ser Ser Ala His Leu Met Ile
    50                  55                  60 cga cac agt ggc atc atc gag gaa ctc gga ctc ggc gcg cac ggc ctt     240
Arg His Ser Gly Ile Ile Glu Glu Leu Gly Leu Gly Ala His Gly Leu
65                  70                  75                  80 cgc tac atc gac tgt gac ccg tgg gcg ttc gct ccg ccc gcc cct ggc     288
Arg Tyr Ile Asp Cys Asp Pro Trp Ala Phe Ala Pro Pro Ala Pro Gly
                85                  90                  95 acc gac ggg ccg ggc atc gtg ttt cat cgc gac ctc gat gca acc tgc     336
Thr Asp Gly Pro Gly Ile Val Phe His Arg Asp Leu Asp Ala Thr Cys
            100                 105                 110 cag tcc atc gaa cga gct tgc ggg aca aag gac gcc gac gcg tac cgg     384
Gln Ser Ile Glu Arg Ala Cys Gly Thr Lys Asp Ala Asp Ala Tyr Arg
        115                 120                 125 cgg ttc gtc gcg gtc tgg tcg gag cgc agc cga cac gtg ttg aag gca     432
Arg Phe Val Ala Val Trp Ser Glu Arg Ser Arg His Val Leu Lys Ala
    130                 135                 140 ttt tcc aca ccg ccc acc gga tcg aac ctg atc ggt gcg ttc gga gga     480
Phe Ser Thr Pro Pro Thr Gly Ser Asn Leu Ile Gly Ala Phe Gly Gly
145                 150                 155                 160
```

```
                    145                 150                 155                 160
ctg gcc aca gtg cgc ggc aac agc gaa ctg tcg cgg cag ttc ctc gcg     528
Leu Ala Thr Val Arg Gly Asn Ser Glu Leu Ser Arg Gln Phe Leu Ala
                    165                 170                 175 ccg ggc gac gca ctg ctg gac gag tat ttc gac agt gag gta ctc aag     576
Pro Gly Asp Ala Leu Leu Asp Glu Tyr Phe Asp Ser Glu Val Leu Lys
            180                 185                 190 gca gcg ttg gcg tgg ttc ggc gcc cag tcc ggg cct ccg atg tcg gaa     624
Ala Ala Leu Ala Trp Phe Gly Ala Gln Ser Gly Pro Pro Met Ser Glu
        195                 200                 205 ccg gga acc gct ccg atg gtc ggc ttc gcg gcc ctc atg cac gtc ctg     672
Pro Gly Thr Ala Pro Met Val Gly Phe Ala Ala Leu Met His Val Leu
    210                 215                 220 ccg ccc ggg cga gca gtc gga ggg agc ggc gca ctg agt gct gcg ttg     720
Pro Pro Gly Arg Ala Val Gly Gly Ser Gly Ala Leu Ser Ala Ala Leu
225                 230                 235                 240 gca tcc cgg atg gct gtc gac ggc gcc acc gtc gcg ctc ggt gac ggc     768
Ala Ser Arg Met Ala Val Asp Gly Ala Thr Val Ala Leu Gly Asp Gly
                    245                 250                 255 gtg acg tcg atc cgc cgg aac tcg aat cac tgg acc gtc aca acc gag     816
Val Thr Ser Ile Arg Arg Asn Ser Asn His Trp Thr Val Thr Thr Glu
                260                 265                 270 agc ggt cga gaa gtc cac gct cgc aag gta atc gcg ggt tgc cac atc     864
Ser Gly Arg Glu Val His Ala Arg Lys Val Ile Ala Gly Cys His Ile
            275                 280                 285 ctc acg aca ctc gat ctc ctg ggc aac gga ggc ttc gac cga acc aag     912
Leu Thr Thr Leu Asp Leu Leu Gly Asn Gly Gly Phe Asp Arg Thr Lys
        290                 295                 300 ctt gat cac tgg cgg cgg aag atc agg gtc ggc ccc ggc atc ggc gct     960
Leu Asp His Trp Arg Arg Lys Ile Arg Val Gly Pro Gly Ile Gly Ala
305                 310                 315                 320 gta ttg cga ctg gcg aca tct gcg ctc ccg tcc tac cgc ggc gac gcc    1008
Val Leu Arg Leu Ala Thr Ser Ala Leu Pro Ser Tyr Arg Gly Asp Ala
                    325                 330                 335 acg aca cgg gaa agt acc tcg gga ttg caa tta ctc gtt tcc gat cgc    1056
Thr Thr Arg Glu Ser Thr Ser Gly Leu Gln Leu Leu Val Ser Asp Arg
                340                 345                 350 gcc cac ttg cgc act gca cac ggc gca gca ctg gca ggg gaa ctg cct    1104
Ala His Leu Arg Thr Ala His Gly Ala Ala Leu Ala Gly Glu Leu Pro
            355                 360                 365 cct cgc cct gcg gtt ctc gga atg agt ttc agc gga atc gat ccc acg    1152
Pro Arg Pro Ala Val Leu Gly Met Ser Phe Ser Gly Ile Asp Pro Thr
        370                 375                 380 atc gcc ccg gcc ggg cgg cat cag gtg aca ctg tgg tcg cag tgg cag    1200
Ile Ala Pro Ala Gly Arg His Gln Val Thr Leu Trp Ser Gln Trp Gln
385                 390                 395                 400 ccg tat cgt ctc agc gga cat cgc gat tgg gcg tcg gtc gcc gag gcc    1248
Pro Tyr Arg Leu Ser Gly His Arg Asp Trp Ala Ser Val Ala Glu Ala
                    405                 410                 415 gag gcc gac cgg atc gtc ggc gag atg gag gct ttt gca ccc gga ttc    1296
Glu Ala Asp Arg Ile Val Gly Glu Met Glu Ala Phe Ala Pro Gly Phe
                420                 425                 430 acc gat tcc gtc ctc gac cgc ttc att caa act ccc cgc gac atc gag    1344
Thr Asp Ser Val Leu Asp Arg Phe Ile Gln Thr Pro Arg Asp Ile Glu
            435                 440                 445 tcg gaa ttg ggg atg atc ggc gga aat gtc atg cac gtc gag atg tca    1392
Ser Glu Leu Gly Met Ile Gly Gly Asn Val Met His Val Glu Met Ser
        450                 455                 460 ctc gat cag atg atg ttg tgg cga ccg ctt ccc gaa ttg tcc ggc cat    1440
Leu Asp Gln Met Met Leu Trp Arg Pro Leu Pro Glu Leu Ser Gly His
```

-continued

```
Leu Asp Gln Met Met Leu Trp Arg Pro Leu Pro Glu Leu Ser Gly His
465                 470                 475                 480 cgc gtt ccg gga gca gac ggg ttg tat ctg acc gga gcc tcg acg cat    1488
Arg Val Pro Gly Ala Asp Gly Leu Tyr Leu Thr Gly Ala Ser Thr His
                485                 490                 495 ccc ggt ggt ggt gtg tcc gga gcc agt ggt cgc agt gcc gct cga atc    1536
Pro Gly Gly Gly Val Ser Gly Ala Ser Gly Arg Ser Ala Ala Arg Ile
            500                 505                 510 gca ctg tcc gac agc cgc tgg ggt aaa gcg agt cag tgg atg cgt cgt    1584
Ala Leu Ser Asp Ser Arg Trp Gly Lys Ala Ser Gln Trp Met Arg Arg
        515                 520                 525 tcg agc cgc tcg tga                                                1599
Ser Ser Arg Ser
    530
```

<210> SEQ ID NO 22
<211> LENGTH: 532
<212> TYPE: PRT
<213> ORGANISM: artificial sequence
<220> FEATURE:
<223> OTHER INFORMATION: Synthetic Construct

<400> SEQUENCE: 22

```
Met Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Leu Lys Ala
    130                 135                 140

Phe Ser Thr Pro Pro Thr Gly Ser Asn Leu Ile Gly Ala Phe Gly Gly
145                 150                 155                 160

Leu Ala Thr Val Arg Gly Asn Ser Glu Leu Ser Arg Gln Phe Leu Ala
                165                 170                 175

Pro Gly Asp Ala Leu Leu Asp Glu Tyr Phe Asp Ser Glu Val Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270
```

-continued

```
Ser Gly Arg Glu Val His Ala Arg Lys Val Ile Ala Gly Cys His Ile
        275                 280                 285
Leu Thr Thr Leu Asp Leu Leu Gly Asn Gly Gly Phe Asp Arg Thr Lys
        290                 295                 300
Leu Asp His Trp Arg Arg Lys Ile Arg Val Gly Pro Gly Ile Gly Ala
305                 310                 315                 320
Val Leu Arg Leu Ala Thr Ser Ala Leu Pro Ser Tyr Arg Gly Asp Ala
                325                 330                 335
Thr Thr Arg Glu Ser Thr Ser Gly Leu Gln Leu Leu Val Ser Asp Arg
                340                 345                 350
Ala His Leu Arg Thr Ala His Gly Ala Ala Leu Ala Gly Glu Leu Pro
            355                 360                 365
Pro Arg Pro Ala Val Leu Gly Met Ser Phe Ser Gly Ile Asp Pro Thr
        370                 375                 380
Ile Ala Pro Ala Gly Arg His Gln Val Thr Leu Trp Ser Gln Trp Gln
385                 390                 395                 400
Pro Tyr Arg Leu Ser Gly His Arg Asp Trp Ala Ser Val Ala Glu Ala
                405                 410                 415
Glu Ala Asp Arg Ile Val Gly Glu Met Glu Ala Phe Ala Pro Gly Phe
                420                 425                 430
Thr Asp Ser Val Leu Asp Arg Phe Ile Gln Thr Pro Arg Asp Ile Glu
            435                 440                 445
Ser Glu Leu Gly Met Ile Gly Gly Asn Val Met His Val Glu Met Ser
        450                 455                 460
Leu Asp Gln Met Met Leu Trp Arg Pro Leu Pro Glu Leu Ser Gly His
465                 470                 475                 480
Arg Val Pro Gly Ala Asp Gly Leu Tyr Leu Thr Gly Ala Ser Thr His
                485                 490                 495
Pro Gly Gly Gly Val Ser Gly Ala Ser Gly Arg Ser Ala Ala Arg Ile
            500                 505                 510
Ala Leu Ser Asp Ser Arg Trp Gly Lys Ala Ser Gln Trp Met Arg Arg
        515                 520                 525
Ser Ser Arg Ser
        530
```

```
<210> SEQ ID NO 23
<211> LENGTH: 486
<212> TYPE: DNA
<213> ORGANISM: artificial sequence
<220> FEATURE:
<223> OTHER INFORMATION: Mutant crtZ coding sequence from strain
      356M4005
<220> FEATURE:
<221> NAME/KEY: CDS
<222> LOCATION: (1)..(486)

<400> SEQUENCE: 23
```

```
atg tcc tgg ccg acg atg atc ctg ctg ttc ctc gcc acc ttc ctg ggg     48
Met Ser Trp Pro Thr Met Ile Leu Leu Phe Leu Ala Thr Phe Leu Gly
1               5                  10                  15 atg gag gtc ttc gcc tgg gcg atg cat cgc tat gtc atg cac ggc ctg     96
Met Glu Val Phe Ala Trp Ala Met His Arg Tyr Val Met His Gly Leu
                20                  25                  30 ctg tgg acc tgg cac cgc agc cat cat gag ccg cac gac gac gtg ctg    144
Leu Trp Thr Trp His Arg Ser His His Glu Pro His Asp Asp Val Leu
            35                  40                  45 gaa agg aac gac ctg ttc gcg gtg gtg ttc gcc gcc ccg gcc atc atc    192
```

```
                Glu Arg Asn Asp Leu Phe Ala Val Val Phe Ala Ala Pro Ala Ile Ile
                 50                  55                  60 ctc gtc gcc ttg ggt cta cat ctg tgg cct tgg atg ctg ccg atc ggc          240
Leu Val Ala Leu Gly Leu His Leu Trp Pro Trp Met Leu Pro Ile Gly
 65                  70                  75                  80 ctg ggc gtt acg gcc tat gga ctg gtt tat tcc ttc ttt cac gac ggg          288
Leu Gly Val Thr Ala Tyr Gly Leu Val Tyr Ser Phe Phe His Asp Gly
                 85                  90                  95 ctg gtg cat cgc cgg ttc ccg aca ggg atc gca ggg cgc tcg gcg ttc          336
Leu Val His Arg Arg Phe Pro Thr Gly Ile Ala Gly Arg Ser Ala Phe
                100                 105                 110 tgg acg cga cgc att cag gcc cac cgg ctg cat cac gcg gtg cgg aca          384
Trp Thr Arg Arg Ile Gln Ala His Arg Leu His His Ala Val Arg Thr
            115                 120                 125 cgc gag ggc tgc gta tcg ttc ggc ttc ctt tgg ggg cgg tcg gcg cgc          432
Arg Glu Gly Cys Val Ser Phe Gly Phe Leu Trp Gly Arg Ser Ala Arg
        130                 135                 140 gcg ctg aag gcc gaa ctg tct cag aaa cgc ggc tca tcc agc aac ggc          480
Ala Leu Lys Ala Glu Leu Ser Gln Lys Arg Gly Ser Ser Ser Asn Gly
145                 150                 155                 160 gcc tga                                                                  486
Ala <210> SEQ ID NO 24
<211> LENGTH: 161
<212> TYPE: PRT
<213> ORGANISM: artificial sequence
<220> FEATURE:
<223> OTHER INFORMATION: Synthetic Construct

<400> SEQUENCE: 24

Met Ser Trp Pro Thr Met Ile Leu Leu Phe Leu Ala Thr Phe Leu Gly
 1               5                  10                  15

Met Glu Val Phe Ala Trp Ala Met His Arg Tyr Val Met His Gly Leu
                20                  25                  30

Leu Trp Thr Trp His Arg Ser His His Glu Pro His Asp Asp Val Leu
            35                  40                  45

Glu Arg Asn Asp Leu Phe Ala Val Val Phe Ala Ala Pro Ala Ile Ile
 50                  55                  60

Leu Val Ala Leu Gly Leu His Leu Trp Pro Trp Met Leu Pro Ile Gly
 65                  70                  75                  80

Leu Gly Val Thr Ala Tyr Gly Leu Val Tyr Ser Phe Phe His Asp Gly
                 85                  90                  95

Leu Val His Arg Arg Phe Pro Thr Gly Ile Ala Gly Arg Ser Ala Phe
                100                 105                 110

Trp Thr Arg Arg Ile Gln Ala His Arg Leu His His Ala Val Arg Thr
            115                 120                 125

Arg Glu Gly Cys Val Ser Phe Gly Phe Leu Trp Gly Arg Ser Ala Arg
        130                 135                 140

Ala Leu Lys Ala Glu Leu Ser Gln Lys Arg Gly Ser Ser Ser Asn Gly
145                 150                 155                 160

Ala
```

BIOPRODUCTION OF ASTAXANTHIN USING MUTANT CAROTENOID KETOLASE AND CAROTENOID HYDROXYLASE GENES

FIELD OF THE INVENTION

This invention is in the field of microbiology, molecular biology, and the use of carotenoid ketolases and carotenoid hydroxlyases to produce astaxanthin. More specifically, nucleic acid molecules encoding both a CrtO carotenoid ketolase and a CrtZ carotenoid hydroxylase are provided that are characterized by improved astaxanthin production. Methods for recombinant production of astaxanthin using the present nucleic acid molecules are also provided.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Industrial uses of carotenoids include pharmaceuticals, food supplements, animal feed additives and colorants in cosmetics to mention a few.

Because animals are unable to synthesize carotenoids de novo, they must obtain them by dietary means. Thus, manipulation of carotenoid production and composition in plants or bacteria can provide new or improved source for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (IPP). In addition, rare carotenoids with longer or shorter backbones occur in some species of nonphotosynthetic bacteria. The term "carotenoid" actually include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (G. Armstrong, (1999) In *Comprehensive Natural Products Chemistry*, Elsevier Press, volume 2, pp 321–352).

Carotenoid biosynthesis starts with the isoprenoid pathway and the generation of a C5 isoprene unit, isopentenyl pyrophosphate (IPP). IPP is condensed with its isomer dimethylallyl pyrophophate (DMAPP) to form the C10, geranyl pyrophosphate (GPP), and elongated to the C15, farnesyl pyrophosphate (FPP). FPP synthesis is common to both carotenogenic and non-carotenogenic bacteria. Enzymes in subsequent carotenoid pathways generate carotenoid pigments from the FPP precursor and can be divided into two categories: carotene backbone synthesis enzymes and subsequent modification enzymes. The backbone synthesis enzymes include geranyl geranyl pyrophosphate synthase, phytoene synthase, phytoene dehydrogenase and lycopene cyclase, etc. The modification enzymes include ketolases, hydroxylases, dehydratases, glycosylases, etc.

Unlike genes in the upstream isoprenoid pathway that are common in all organisms, the downstream carotenoid modifying enzymes are less common.

Carotenoid hydroxylases are a class of enzymes that introduce hydroxyl groups to the ionone ring of the cyclic carotenoids, such as β-carotene, echinenone, 3'-hydroxyechinenone, β-cryptoxanthin, adonirubin, and canthaxanthin to produce hydroxylated carotenoids. Examples of such carotenoids include astaxanthin, β-cryptoxanthin, zeaxanthin, 3-hydroxyechinenone, 3'-hydroxyechinenone, adonirubin, adonixanthin, tetrhydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, and lutein.

Several classes of carotenoid hydroxylases have been reported (i.e. CrtR-type and CrtZ-type). Both CrtR and CrtZ enzymes catalyze addition of hydroxyl groups to the β-ionone rings of cyclic carotenoids. However, no significant sequence homology exists between CrtR hydroxylases and the CrtZ hydroxylases. The CrtR-type carotenoid hydroxylases have been reported in Cyanobacteria such as *Synechocystis* sp. PCC 6803 (Lagarde, D., and Vermaas, W., *FEBS Lett.*, 454(3):247–251 (1999) and in plants. The CrtZ-type carotenoid hydroxylases have been reported from a variety of bacterial, fungal, algal, and plant species. Examples include, but are not limited to, bacterial species such as *Pantoea stewartii* (WO 03/016503; WO 02/079395), *Erwinia uredovora* (EP 393690 B1; Misawa et al., *J. Bacteriol.*, 172(12):6704–6712 (1990)), *Erwinia herbicola* (Hundle et al., *Mol. Gen Genet.*, 245(4):406–416 (1994); Hundle et al., *FEBS Lett.* 315(3):329–334 (1993); Schnurr et al., *FEMS Microbiol. Lett.*, 78(2–3):157–161 (1991); and U.S. Pat. No. 5,684,238), *Agrobacterium aurantiacum* (Misawa et al., *J. Bacteriol.*, 177(22):6575–6584 (1995); U.S. Pat. No. 5,811,273), *Alcaligenes* sp. (U.S. Pat. No. 5,811,273), *Flavobacterium* sp. (U.S. Pat. No. 6,677,134; U.S. Pat. No. 6,291,204; US 2002147371; WO 2004029275; and Pasamontes et al., *Gene*, 185(1):35–41 (1997)), *Paracoccus* sp. (CN 1380415), *Haematococcus pluvialis* (WO 00/061764; Linden, H., *Biochimica et Biophysica Acta*, 1446(3):203–212 (1999)), *Brevundimonas vesicularis* DC263 (U.S. Ser. No. 60/601,947), Enterobacteriaceae strain DC260 (U.S. Ser. No. 10/808,979, and plant species such as *Arabidopsis thaliana* (Tian, L. and DellaPenna, D., *Plant Mol. Biol.*, 47(3):379–388 (2001); US 2002102631).

Carotenoid ketolases are enzymes that introduce keto groups to the β-ionone ring of the cyclic carotenoids, such as β-carotene, echinenone, β-cryptoxanthin, adonixanthin, 3'-hydroxyechinenone, 3-hydroxyechinenone, and zeaxanthin to produce ketocarotenoids. Examples of ketocarotenoids include, but are not limited to astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone.

Several classes of carotenoid ketolases have been reported (Hannibal et al., *J. Bacteriol.*, 182: 3850–3853 (2000)). These include CrtW ketolases from *Agrobacterium aurantiacum* (Misawa et al., *J. Bacteriol.*, 177(22):6575–6584 (1995); WO 99/07867), *Bradyrhizobium* sp. ORS278 (Hannibal et al., *J. Bacteriol.*, 182(13):3850–3853 (2000)), *Brevundimonas aurantiaca* (De Souza et al., WO 02/79395), *Paracoccus marcusii* (Yao et al., CN1380415); Bkt ketolases from *Haematococcus pluvialis* (Sun et al., *Proc. Natl. Acad. Sci.* USA, 95(19):11482–11488 (1998); Linde, H. and Sandmann, G., EP1173579; Breitenbach et al., *FEMS Microbiol. Lett.*, 404(2–3):241–246 (1996)); and CrtO ketolases from *Synechocystis* sp. (Lagarde et al., *Appl. Environ. Microbiol.*, 66(1):64–72 (2000); Masamoto et al., *Plant Cell Physiol.*, 39(5):560–564 (2000); FR 2792335; Cheng et al., WO 03/012056 corresponding to U.S. Ser. No. 10/209, 372)), *Rhodococcus erythropolis* (Cheng et al., supra), *Deinococcus radiodurans* (Cheng et al., supra), and *Gloeobacter violaceus* (Nakamura et al., *DNA Res.*, 10:181–201 (2003)). It should be noted that the CrtO ketolase reported in *Haematococcus pluvialis* (Harker, M. and Hirschberg, J., *FEBS Lett.*, 404(2–3):129–134 (1997); U.S. Pat. No. 5,965, 795; U.S. Pat. No. 5,916,791; and U.S. Pat. No. 6,218,599) appears to be a CrtW/Bkt-type ketolase based on the size (nucleotide coding sequence length <1000 bp) and homology to other CrtW/Bkt ketolases. Bkt ketolases appear to be closely related to CrtW ketolases, sharing very little structural similarity to the CrtO ketolases based on nucleotide and amino acid sequence comparisons (Cheng, et al, supra). For example, a search of the publicly available sequences using the *Haematococcus pluvialis* Bkt ketolase sequence returned matches that most closely matched other CrtW-type ketolases. CrtW/Bkt ketolases are generally encoded by nucleic acid fragments about 800–1000 bp in length, while CrtO ketolases are normally encoded by a nucleic acid fragments of about 1.6 kb in size. Cheng et al. defines CrtO ketolases based on the existence of six conserved motifs considered diagnostic for all CrtO ketolases. The reported CrtO ketolases from *Rhodococcus erythropolis*, *Deinococcus radiodurans*, and *Synechocystis* sp. PCC6803 are comprised of these diagnostic motifs (U.S. Ser. No. 10/209,372).

The wildtype CrtO ketolases reported by Cheng et al. generally exhibit much lower activity when producing ketocarotenoids (i.e. canthaxanthin) from β-carotene in comparison to the reported CrtW ketolases (U.S. Ser. No. 10/209, 372). U.S. Ser. No. 10/209,372 reports that, the use of recombinatly expressed *R. erythropolis* AN12 CrtO ketolase resulted in only 30% conversion of the initial substrate (β-carotene) into canthaxanthin (35% of the initial β-carotene was converted to echinenone with the remaining 35% remaining as β-carotene).

For biosynthesis of astaxanthin, a carotenoid ketolase and a carotenoid hydroxylase have to interact efficiently (Steiger, S. and Sandmann, G., *Biotechnol Lett.*, 26:813–817 (2004)). As shown in FIG. 1, many carotenoid ketolases and carotenoid hydroxylases exhibit some level of substrate flexibility. This leads to a variety of possible enzymatic reactions (producing various intermediates from β-carotene) that may be necessary to produce astaxanthin. Depending upon the activity and substrate specificity of both the ketolase and hydroxylase used, it is often difficult to predict those combinations that will result in optimal production of astaxanthin. For example, it has been reported that hydroxylases from cyanobacteria are not able to accept echinenone or canthaxanthin as substrates for hydroxylation. Conversely, certain ketolases have been reported to be unable to use hydroxylated carotenoids, such as zeaxanthin, as suitable substrates (Steiger and Sandmann, supra). Coexpression of a carotenoid ketolase and a carotenoid hydroxylase that are able to efficiently work together is crucial for producing substantial amounts of astaxathin in a recombinant host cell. When using a recombinant host cell capable of producing suitable amounts of β-carotene, one must take into account a variety of variables that factor into optimal astaxanthin production including, but not limited to 1) substrate flexibility associated with each ketolase and the hydroxylase used, 2) the ability of each enzyme to efficiently hydroxylate/ketolate one or more of the possible carotenoid substrates, and 3) the relative balance of ketolase and hydroxylase enzymatic activity. For example, one can invision a scenario where a ketolase, which selectively uses β-carotene as a substrate, should not be coexpressed with a hydroxylase having much higher activity for β-carotene. In such an instance, the majority of the β-carotene would be expected to be converted into hydroxylated carotenoids (such as zeaxanthin) that may not be recognized by the ketolase, resulting in less than optimal production of astaxanthin.

The CrtO ketolase from *R. erythropolis* AN12 has been protein engineered for increased canthaxanthin production (U.S. Ser. No. 60/577,970). Coexpression of the CrtO ketolase with a CrtZ cartenoid hydroxylase was expected to result in the production of astaxanthin (FIG. 1). However, as described in the present disclosure, coexpression of the best canthaxanthin producing CrtO ketolase mutant ("320SHU001" herein referred to as "crtO-SHU0001") from U.S. Ser. No. 60/577,970 with several different CrtZ hydroxylases did not result in the expected production of astaxanthin.

The problem to be solved is to provide nucleic acid molecules encoding at least one CrtO ketolase and at least one CrtZ hydroxylase that can efficiently work together to produce astaxanthin in a recombinant host cell. A further problem to be solved is to provide a method to produce matched pairs of carotenoid ketolases and carotenoid hydroxylases having astaxanthin biosynthesis activity.

The stated problem has been solved by providing several CrtO ketolase/CrtZ hydroxylase mutants exhibiting improved astaxanthin production in the context of a carotenoid biosynthetic pathway. A nucleic acid fragment (comprised of crtOZ genes) encoding enzymes incapable of producing more than trace amounts astaxanthin was protein engineered using errror-prone PCR to create several CrtO/Z combinations having the ability to produce significant amounts of astaxanthin when expressed in a recombinant host cell. Methods to produce and/or alter astaxanthin production in recombinant host cells using the present genes are also provided.

Additionally, a method to produce combinations of carotenoid ketolases and carotenoid hydroxylases having improved astaxanthin biosynthesis activity is also provided. The method is comprised of simultaneously mutating nucleic acid fragments encoding one or more carotenoid ketolases and one or more carotenoid hydroxylases and screening recombinants for improvements in astaxanthin production.

SUMMARY OF THE INVENTION

The present invention provides nucleic acid molecules encoding CrtO ketolases and CrtZ hydroxylases useful for producing astaxanthin in recombinant host cells engineered to produce β-carotene. A crtOZ gene combination encoding enzymes incapable of producing significant amounts of astaxanthin was simultaneously mutated using error-prone PCR, creating several mutant CrtO/Z enzyme pairs capable of producing increased amounts of astaxanthin.

Accordingly the invention provides an isolated nucleic acid molecule encoding at least one carotenoid ketolase and at least one carotenoid hydroxylase, said nucleic acid molecule comprising:

a) a nucleic acid fragment encoding a carotenoid ketolase having an amino acid sequence selected from the group consisting of SEQ ID NO: 17 and SEQ ID NO: 22; and b) a isolated nucleic acid fragment encoding a carotenoid hydroxylase having an amino acid sequence selected from the group consisting of SEQ ID NO: 19 and SEQ ID NO: 24: or an isolated nucleic acid molecule completely complementary to the nucleic acid molecule comprising the elements of (a) and (b).

In similar fashion the invention provides an isolated nucleic acid molecule encoding at least one carotenoid ketolase and at least one carotenoid hydroxylase, said nucleic acid molecule comprising:
  a) a nucleic acid fragment encoding a carotenoid ketolase having a nucleic acid sequence selected from the group consisting of SEQ ID NO: 16 and SEQ ID NO: 21; and
  b) a nucleic acid fragment encoding a carotenoid hydroxylase having a nucleic acid sequence selected from the group consisting of SEQ ID NO: 18 and SEQ ID NO: 23; or an isolated nucleic acid molecule completely complementary to the nucleic acid molecule comprising the elements of (a) and (b).

Alternatively the invention provides an isolated nucleic acid molecule encoding a carotenoid ketolase and a carotenoid hydroxylase, said isolated nucleic acid molecule comprising:
  a) a nucleic acid fragment encoding a carotenoid ketolase having an amino acid sequence as represented by SEQ ID NO: 17 and
  b) a nucleic acid fragment encoding a carotenoid hydroxylase enzyme having an amino acid sequence as represented by SEQ ID NO: 19; or an isolated nucleic acid molecule completely complementary to the nucleic acid molecule comprising the elements of (a) and (b).

In another embodiment the invention provides an isolated nucleic acid molecule encoding a carotenoid ketolase and a carotenoid hydroxylase, said isolated nucleic acid molecule comprising:
  a) a nucleic acid fragment encoding a carotenoid ketolase having an amino acid sequence as represented by SEQ ID NO: 21; and
  b) a nucleic acid fragment encoding a carotenoid hydroxylase enzyme having an amino acid sequence as represented by SEQ ID NO: 23; or an isolated nucleic acid molecule completely complementary to the nucleic acid molecule comprising the elements of (a) and (b).

In other embodiment the invention provides polypeptides encoded by the instant sequences, genetic chimera of the instant sequences, and host cells transformed with the same.

In one embodiment the invention provides a method for the production of astaxanthin comprising:
  a) providing a transformed host cell that produces β-carotene and which comprises the chimeric gene cluster of the invention encoding at least one carotenoid ketolase enzyme and at least one carotenoid hydroxylase enzyme; and
  b) growing the transformed host cell of (a) under suitable conditions whereby astaxanthin is produced.

Similarly the invention provides a method of altering astaxanthin biosynthesis in an organism comprising:
  a) providing a host cell capable of producing astaxanthin;
  b) introducing into said host cell the nucleic acid molecule of the invention; wherein said nucleic acid molecule encodes a carotenoid ketolase gene and a carotenoid hydroxylase gene; and
  c) growing the host cell of (b) under conditions whereby the nucleic acid molecule is expressed and astaxanthin biosynthesis is altered.

In an other embodiment the invention provides a method to generate and identify nucleic acid molecules encoding a carotenoid ketolase and a carotenoid hydroxylase having improved astaxanthin biosynthesis activity comprising:
  a) providing a host cell capable of producing β-carotene;
  b) providing a starting pair of genes comprising a carotenoid ketolase gene and a carotenoid hydroxylase;
  c) exposing said starting pair of genes simultaneously to mutational conditions in vitro to form a mutated gene pair; wherein at least one nucleotide has been altered in either one or both of said carotenoid ketolase gene or said carotenoid hydroxylase gene;
  d) operably linking the mutated gene pair to a suitable regulatory sequence;
  e) transforming the host cell of step a) with the mutated gene pair from step d) to produce a recombinant host cell;
  f) growing the recombinant host cell under conditions whereby astaxanthin is produced;
  g) measuring the amount of astaxanthin produced in step f) and selecting those transformants having increased astaxanthin production relative to the level of astaxanthin produced by the starting pair of genes in the host cell; and
  h) identifying the mutated gene pair from the selected transformants which have increased astaxanthin biosynthesis activity.

BRIEF DESCRIPTION OF THE FIGURES BIOLOGICAL DEPOSITS AND SEQUENCE DESCRIPTIONS

The invention can be more fully understood from the following figure, detailed description, biological deposits, and the accompanying sequence descriptions, which form a part of this application.

FIG. 1 shows common carotenoid products produced by carotenoid ketolases in conjunction with carotenoid hydroxylase enzymes using β-carotene as the substrate.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleotide sequence of a mutant crtO carotenoid ketolase coding sequence, designated as "crtO-SHU001", previously created by protein engineering the wild type crtO gene from *Rhodococcus erythropolis* AN12 for improved ketocarotenoid production (U.S. Ser. No. 60/577,970).

SEQ ID NO: 2 is deduced amino acid sequence of crtO-SHU001.

SEQ ID NO: 3 is the nucleotide sequence of primer crtO-SHU001-F.

SEQ ID NO: 4 is the nucleotide sequence of primer crtO-SHU001-R.

SEQ ID NO: 5 is the nucleotide sequence of the crtZ hydroxylase coding sequence isolated from *Brevundimonas vesicularis* DC263 (U.S. Ser. No. 60/601,947).

SEQ ID NO: 6 is the deduced amino acid sequence of the CrtZ hydroxylase from *Brevundimonas vesicularis* DC263 (U.S. Ser. No. 60/601,947).

SEQ ID NO: 7 is the nucleotide sequence of primer crtZ-263_F2.

SEQ ID NO: 8 is the nucleotide sequence of primer crtZ-263_R2.

SEQ ID NO: 9 is the nucleotide sequence of the crtZ hydroxylase coding sequence isolated from Enterobacteriaceae DC260 (U.S. Ser. No. 10/808,979).

SEQ ID NO: 10 is the deduced amino acid sequence of the CrtZ hydroxylase isolated from Enterobacteriaceae DC260 (U.S. Ser. No. 10/808,979).

SEQ ID NO: 11 is the nucleotide sequence of primer crtZ-DC260-F.

SEQ ID NO: 12 is the nucleotide sequence of primer crtZ-DC260-R.

SEQ ID NO: 13 is the nucleotide sequence of primer 334F1.

SEQ ID NO: 14 is the nucleotide sequence of primer 334R1.

SEQ ID NO: 15 is the nucleotide sequence of the nucleic acid fragment comprised of the mutant crtOZ coding sequences found in plasmid pDCQ356M4003.

SEQ ID NO: 16 is the nucleotide sequence of the crtO ketolase coding sequence found in plasmid pDCQ356M4003.

SEQ ID NO: 17 is the deduced amino acid sequence of the mutant CrtO ketolase from plasmid pDCQ356M4003.

SEQ ID NO: 18 is the nucleotide sequence of the crtZ hydroxylase coding sequence found in plasmid pDCQ356M4003.

SEQ ID NO: 19 is the deduced amino acid sequence of the mutant CrtZ hydroxylase from plasmid pDCQ356M4003.

SEQ ID NO: 20 is the nucleotide sequence of the nucleic acid fragment comprised of the mutant crtOZ coding sequence from plasmid pDCQ356M4005.

SEQ ID NO: 21 is the nucleotide sequence of the mutant crtO ketolase coding sequence found in plasmid pDCQ356M4005.

SEQ ID NO: 22 is the deduced amino acid sequence of the mutant CrtO ketolase from plasmid pDCQ356M4005.

SEQ ID NO: 23 is the nucleotide sequence of the mutant crtZ hydroxylase coding sequence from plasmid pDCQ356M4005.

SEQ ID NO: 24 is the deduced amino acid sequence of the mutant CrtZ hydroxylase from plasmid pDCQ356M4005.

BRIEF DESCRIPTION OF THE BIOLOGICAL DEPOSIT

The following biological deposit has been made under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Methylomonas 16a | ATCC# PTA-2402 | Aug. 22, 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The invention relates to nucleic acid molecules encoding CrtO ketolases and CrtZ hydroxylases useful for astaxanthin production. Coexpression of the present crtOZ genes in a recombinant host cell resulted in a significant increase in astaxanthin production. In another embodiment, methods to produce and/or alter astaxanthin production in a recombinant host cell using the present crtOZ genes are also provided. In yet a further embodiment, a method to produce matched carotenoid ketolase and carotenoid hydroxylase having an improvement in astaxanthin production is also provided.

In this disclosure, a number of terms and abbreviations are used. The following definitions are provided.

As used herein, the term "comprising" means the presence of the stated features, integers, steps, or components as referred to in the claims, but that it does not preclude the presence or addition of one or more other features, integers, steps, components or groups thereof.

"Open reading frame" is abbreviated ORF.

"Polymerase chain reaction" is abbreviated PCR.

As used herein, the terms an "isolated nucleic acid fragment" and "an isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to the compounds are any molecule derived from the isoprenoid pathway including 10 carbon terpenoids and their derivatives, such as carotenoids and xanthophylls.

The term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

The term "carotenoid ketolase" or "ketolase" refers to an enzyme that can add keto groups to the ionone ring of either monocyclic or bicyclic carotenoids. Two distinct classes of carotenoid ketolase have been reported. The first class will be referred to as the CrtW/Bkt-type ketolase and are generally encoded by a nucleotide sequence of approximately 800–1000 bp in length. The second class of ketolase is the CrtO-type ketolase. The CrtO-type ketolase is normally encoded by nucleotide sequence of approximately 1.6 kb in length and exhibits no structural similarity to the CrtW/Bkt ketolases (See U.S. Ser. No. 60/577,970).

The terms "crtO-SHU001" and "320SHU001" will be used interchangeably and refer to the nucleic acid fragment encoding a mutant CrtO ketolase previously engineered for increased ketocarotenoid (i.e. canthaxanthin) production (U.S. Ser. No. 60/577,970; hereby incorporated by reference). The crtO-SHU001 gene (SEQ ID NO: 1) was used as the starting gene for error-prone PCR reactions to create crtOZ combinations having the ability to produce significant amounts of astaxanthin.

The term "carotenoid hydroxylase" or "hydroxylase" or "CrtZ hydroxylase" refers to an enzyme that adds hydroxyl groups to the ionone ring of either monocyclic or bicyclic carotenoids. Two CrtZ hydroxylases (crtZ from *Brevundimonas vesicularis* DC263; U.S. Ser. No. 60/601,947 and crtZ from Enterobacteriaceae DC260; U.S. Ser. No. 10/808,979; both incorporated herein by reference) were individually coexpressed with a CrtO ketolase (crtO-SHU001) to determine if either crtOZ combination could produce astaxanthin in *E. coli* or *Methylomonas* 16a. Neither of the CrtZ hydroxylases coexpressed with crtO-SHU001 could produce astaxanthin in significant amounts. The CrtO ketolase gene crtO-SHU001 and the crtZ gene (SEQ ID NO: 5) from *Brevundimonas vesicularis* DC263 were selected and used as the starting genes for simultaneous error-prone PCR experiments used to create crtOZ combinations (SEQ ID NOs: 15 and 20) having the ability to produce significant amounts of astaxanthin.

The term "crtO/Z" will refer to an isolated nucleic acid molecule encoding polypeptide(s) having carotenoid hydroxylase and carotenoid ketolase activity as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp, *CABIOS*, 5:151–153 (1989)) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

"Codon degeneracy" refers to the nature in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs: 19, 22, and 24 The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "conservative substitution" is used to describe alterations in a gene which result in the production of a chemically equivalent amino acid at a given site, but do not effect the functional properties of the encoded protein are common. For the purposes of the present invention, substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. In another embodiment, the present nucleic acid fragments may optionally include those having conservative substitutions.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available. For example, the preferred codon usage for *Methylomonas* sp. 16a (ATCC PTA-2402) has been previously reported in U.S. Ser. No. 60/527,083; hereby incorporated by reference.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal (normally limited to eukaryotes) is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. As used herein, the host cell genome includes both chromosomal or extrachromosomal (i.e. a vector) genes with the host cell. Host organisms containing the transformed nucleic acid fragments are referred to as "transgenic" or "recombinant" or "transformed" organisms.

The terms "*Rhodococcus erythropolis* AN12", "*Rhodococcus erythropolis* strain AN12" or "AN12" will be used interchangeably and refer to the *Rhodococcus erythropolis* AN12 strain (U.S. Ser. No. 10/209,372).

The terms "*Brevundimonas vesicularis*" and "*Brevundimonas vesicularis* strain DC263" will be used interchangeably and refer to the *Brevundimonas vesicularis* DC263 strain (U.S. Ser. No. 60/601,947).

The term "Enterobacteriaceae DC260" or "DC260" will be used interchangeably and refer to the Enterobacteriaceae DC260 strain (U.S. Ser. No. 10/808,979).

The term "pDCQ334" refers to a plasmid comprised of the crtWZEidiYIB gene cluster capable of producing astaxanthin in a recombinant host cell (U.S. Ser. No. 60/527,083). The plasmid was created by cloning a codon optimized version (optimized for *Methylomonas* sp. 16a) of the *Agrobacterium aurantiacum* crtWZ genes (U.S. Pat. No. 5,972, 690; GenBank® D58420) upstream of crtE in the native crtEidiYIB cluster from *P. agglomerans* DC404 (U.S. Ser. No. 10/808,807) to form the operon crtWZEidiYIB (U.S.

Ser. No. 60/527,083). The crtWZEidiYIB genes were organized in an operon and were under the control of the chloramphenicol resistant gene promoter of the parent vector (broad host range vector pBHR1; MoBiTec, LLC, Marco Island, Fla.).

The term "pDCQ353" refers to the plasmid comprised of the crtO-SHU001 gene cloned into a pTrcHis2-TOPO vector (Invitrogen, Carlsbad, Calif.).

The term "pDCQ354" refers the plasmid created by replacing the crtWZ gene cluster in pDCQ334 with a nucleic acid fragment comprised of the crtO-SHU001 gene, resulting in the operon crtOEidiYIB. Recombinant cells containing pDCQ354 produce canthaxanthin.

The term "pDCQ352" refers to the plasmid created by cloning the crtZ gene from Brevundimonas vesicularis strain DC263 into a pTrcHis2-TOPO vector.

The term "pDCQ355" refers to the plasmid created by cloning the crtZ gene from Enterobacteriaceae DC260 into a pTrcHis2-TOPO vector.

The term "pDCQ356" refers to the plasmid created by cloning the crtZ gene from Brevundimonas vesicularis strain DC263 into the SpeI restriction site of pDCQ354, resutling in the operon crtOZEidiYIB. Transformants harboring pDCQ356 were unable to produce significant amounts of astaxanthin. Plasmid pDCQ356 was selected as the "control" plasmid used to evaluate various mutant crtOZ gene clusters for their ability to produce astaxanthin. The crtOZ gene cluster from pDCQ356 was used as a template for error-prone PCR.

The term "pDCQ357" refers to the plasmid created by cloning the crtZ gene from Enterobacteriaceae DC260 into the SpeI restriction site of pDCQ354, resulting in the operon crtOZEidiYIB. Transformants harboring pDCQ357 were unable to produce significant amounts of astaxanthin.

The term "pDCQ356M4003" refers to a plasmid created by removing the crtOZ insert from pDCQ356 and inserting a mutagenized crtOZ gene cluster. The mutant CrtO was comprised on an amino acid sequence as shown in SEQ ID NO: 17. The mutant CrtZ was comprised of an amino acid sequence as shown in SEQ ID NO: 19. Transformants harboring pDCQ356M4003 were able to produce significant amounts of astaxanthin.

The term "pDCQ356M4005" refers to a plasmid created by removing the crtOZ insert from pDCQ356 and inserting a mutagenized crtOZ gene cluster. The mutant CrtO was comprised on an amino acid sequence as shown in SEQ ID NO: 22. The mutant CrtZ was comprised of an amino acid sequence as shown in SEQ ID NO: 24. Transformants harboring pDCQ356M4005 were able to produce significant amounts of astaxanthin.

The term "carbon substrate" refers to a carbon source capable of being metabolized by host organisms of the present invention and particularly carbon sources selected from the group consisting of monosaccharides, disaccharides, polysaccharides, and one-carbon substrates or mixtures thereof. In one embodiment, the carbon substrate is a single carbon substrate selected from the group consisting of methane and/or methanol.

The term "Entner-Douderoff pathway" refers to a series of biochemical reactions for conversion of hexoses such as glucose or fructose to the important 3-carbon cellular intermediates pyruvate and glyceraldehyde 3-phosphate without any net production of biochemically useful energy. The key enzymes unique to the Entner-Douderoff pathway are the 6-phosphogluconate dehydratase and a ketodeoxyphosphogluconate aldolase.

The term "Embden-Meyerhof pathway" refers to the series of biochemical reactions for conversion of hexoses such as glucose and fructose to important cellular 3-carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerhof pathway are the phosphofructokinase and fructose 1,6 bisphosphate aldolase.

The term "$C_1$ carbon substrate" or "single carbon substrate" refers to any carbon-containing molecule that lacks a carbon—carbon bond. Examples are methane, methanol, formaldehyde, formic acid, formate, methylated amines (e.g., mono-, di-, and tri-methyl amine), methylated thiols, and carbon dioxide. In another embodiment, the $C_1$ carbon substrate is methanol and/or methane.

The term "$C_1$ metabolizer" refers to a microorganism that has the ability to use a single carbon substrate as its sole source of energy and biomass. $C_1$ metabolizers will typically be methylotrophs and/or methanotrophs.

The term "methylotroph" means an organism capable of oxidizing organic compounds that do not contain carbon—carbon bonds. Where the methylotroph is able to oxidize $CH_4$, the methylotroph is also a methanotroph. In another embodiment, the methylotroph is capable of using methanol and/or methane as a carbon source.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera Methylomonas, Methylobacter, Methylococcus, and Methylosinus.

The term "high growth methanotrophic bacterial strain" refers to a bacterium capable of growth with methane or methanol as the sole carbon and energy source and which possesses a functional Embden-Meyerof carbon flux pathway resulting in a high rate of growth and yield of cell mass per gram of $C_1$ substrate metabolized. The specific "high growth methanotrophic bacterial strain" described herein is referred to as "Methylomonas 16a", "16a" or "Methylomonas sp. 16a", which terms are used interchangeably and which refer to the Methylomonas sp. 16a (ATCC PTA-2402) strain (U.S. Pat. No. 6,689,601) and derivatives thereof which possess a functional Embden-Meyerof carbon flux pathway.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

In the present application, matched pairs of protein engineered CrtO ketolases and CrtZ hydroxylases are provided that have improved "astaxanthin biosynthesis activity" when compared the genes from which they were developed. In the present application the crtO gene was the mutant "crtO-SHU0001" and was previously engineered for increased ketocaroenoid production; see U.S. Ser. No. 60/577,970). "Astaxanthin biosynthesis activity" refers to the amount of astaxanthin produced under specified conditions in a recombinant host cell. Improved astaxanthin biosynthesis activity is determined by comparing the activity of mutant genes expressed in a host cell and function in the context of an existing or engineered carotenoid enzymatic pathway with the expression of the genes from which they were derived functioning in the same host cell under the same conditions. Thus in the present application increases in astaxanthin biosynthesis activity were measured by comparing the amount of astaxanthin produced by mutant crtO/Z gene(s) versus the astaxanthin biosynthesis activity of host cells expressing the crtOZ genes from plasmid pDCQ356 (original genes) under identical reaction conditions. The matched pair of enzymes (CrtO and CrtZ) expressed from pDCQ356 (i.e. the "starting genes") exhibited insignificant astaxanthin production when expressed in a recombinant host cell capable of producing β-carotene. The expression system used to evaluate each mutant and the corresponding control was identical. The recombinant protein expression level of each mutant crtOZ pair was essentially identical. Improvements in the percentage yield of astaxanthin production were attributed to structural differences associated with the CrtO ketolase and/or CrtZ hydroxylase. The crtOZ coding sequences were simulatenous mutated using error-prone PCR to produce a matched gene pair that optimally produces astaxanthin. In another embodiment, the present mutant crtO genes or crtZ genes may be individually matched and recombinantly expressed with other carotenoid ketolases and/or hydroxylases for the production of astaxanthin. The structural differences are represented by the nucleotide and amino acid sequences provided herein.

The term "mutational conditions" refers to conditions that result in gene mutations. Typical mutational conditions will include the conditions prescribed by error Prone PCR ((Melnikov et al., *Nucleic Acids Research,* 27(4):1056–1062 (1999); Leung et al., *Techniques,* 1:11–15 (1989); and Zhou et al., *Nucleic Acids Res.,* 19:6052–6052 (1991)); and methods of gene schuffling (see for example U.S. Pat. No. 5,605,793; U.S. Pat. No. 5,811,238; U.S. Pat. No. 5,830,721; and U.S. Pat. No. 5,837,458; and Tang et al., U.S. Ser. No. 10/374,366; and Ikeuchi et al., *Biotechnol. Prog.,* 2003, 19 1460–7).

"Amplification" is the process in which replication is repeated in cyclic manner such that the number of copies of the "template nucleic acid" is increased in either a linear or logarithmic fashion.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) the FASTA program incorporating the Smith-Waterman algorithm (W. R. Pearson, *Comput. Methods Genome Res.,* [Proc. Int. Symp.] (1994), Meeting Date 1992, 111–20. Editor(s): Suhai, Sandor. Plenum: New York, N.Y.); and 5.) the Vector NTI version 7.0 programs (Informax, Inc., Bethesda, Md.). Within the context of this application it will be understood that where sequence analysis software is used for analysis, that the results of the analysis will be based on the "default values" of the program referenced, unless otherwise specified. As used herein "default values" will mean any set of values or parameters (set by the manufacturer) which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

The present invention provides several mutant crtOZ genes having the ability to produce significant amounts of astaxanthin when compared to the astaxanthin synthesizing activity of the "starting genes" (exemplified herein using the crtO-SHU001 gene (SEQ ID NO: 1) coexpressed with the crtZ gene (SEQ ID NO: 5) from *Brevundimonas vesicularis* DC263). Improvements in astaxanthin synthesis were conducted in recombinant hosts engineered to produce suitable amounts of β-carotene. Improvements in astaxanthin synthesis were determined by comparing the percentage yield of astaxanthin in the various mutants produced to the activity of the "starting genes".

In one embodiment, paired CrtO/Z enzymes of the present invention are those having an increase in the percentage yield of astaxanthin of at least 5% when compared to the percentage yield of astaxanthin in recombinant hosts coexpressing the crtO-SHU001 ketolase gene and the crtZ hydroxylase gene from *Brevundimonas vesicularis* DC263 under identical reaction conditions. More preferred CrtO/Z enzyme pairs of the present invention are those exhibiting at least a 10% increase in the percentage yield of astaxanthin when coexpressed in a recombinant host cell. Even more preferred CrtO/Z enzyme pairs are those exhibiting at a 20% increase in the percentage yield of astaxanthin. Comparisons in astaxanthin synthesizing activity can be conducted under a variety of reaction conditions depending upon the selected host organism. Suitable comparisons are those conducted between the engineered crtOZ gene pair of interest and a suitable control (i.e. another crtOZ gene cluster) recombinantly expressed (using identical expression systems) under identical reaction conditions (i.e. recombinant host cells capable of producing suitable levels of β-carotene). In a further embodiment, "significant astaxanthin production" will be used to described recombinant production of astaxanthin where at least about 3% of the total carotenoids produced is astaxanthin, preferably at least about 5%, more preferably at least about 15%, and most preferably at least about 20%.

In one embodiment, a method to produce matched pairs of carotenoid ketolase(s) and carotenoid hydroxylase(s) for increased or optimized production of astaxanthin is also provided.

In another embodiment, the process to produced carotenoid ketolases and carotenoid hydroxylases having an improved ability to produce astaxanthin is not limited to CrtO-type carotenoid ketolases or CrtZ carotenoid hydroxylases. The method comprises 1) providing a recombinant host cell capable of producing β-carotene, 2) providing at least one carotenoid ketolase and at least one carotenoid hydroxylase (i.e. "starting genes"), 3) simulatenously treating the genes encoding at least one carotenoid ketolase and at least one carotenoid hydroxylase using a mutagenizing process or under mutational conditions, 4) transforming the recombinant host cell with the mutated genes, 5) screening the recombinant host cell for increased astaxanthin production relative to recombinant host cells expressing the starting genes, and 6) selecting those recombinant hosts with increased astaxanthin production, and optionally isolating the mutated gene pair and optionally repeating steps 1) through step 6).

The present CrtO/Z ketolase/hydroxylase pairs may be used in vitro or in vivo in for the production of astaxanthin from β-carotene and/or intermediates in the synthesis of astaxanthin as shown in FIG. 1.

Recombinant Expression of crtO/Z—Microbial

The genes and gene products of the instant sequences may be used in heterologous host cells, particularly in the cells of microbial hosts, for the production of carotenoid compounds and particularly for the production of astaxanthin.

Preferred heterologous host cells for expression of the present mutant crtO/Z genes are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of potential host strains include, but are not limited to bacterial, fungal or yeast genera such as *Aspergillus, Trichoderma, Saccharomyces, Pichia, Phaffia, Candida, Hansenula*, or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, the host strain is a methylotroph grown on methanol and/or methane. Preferred bacterial species include *Escherichia coli, Methylomonas* sp. 16a, and derivatives thereof.

Microbial expression systems and expression vectors containing regulatory sequences that direct high-level expression of foreign proteins are well known to those skilled in the art. Any of these could be used to construct chimeric genes for expression of present CrtO ketolases and/or CrtZ hydroxylases. These chimeric genes could then be introduced into appropriate microorganisms via transformation to provide high-level expression of the present enzymes.

Accordingly, it is expected that introduction of chimeric genes encoding the present bacterial enzymes under the control of the appropriate promoters will demonstrate increased or altered astaxanthin production. It is also contemplated that it will be useful to express the instant genes both in natural ("native") host cells as well as heterologous hosts. Since the combination of a crtO ketolase and a crtZ hydroxylase are typically not coexpressed together in a single native host cell, the term "natural host cell" can be optionally defined to be any host cell where either one of the two genes is naturally expressed. Introduction of the present crtO/Z genes into native host cell will result in altered levels of existing astaxanthin production. Additionally, the instant genes may also be introduced into non-native host bacteria where the existing carotenoid pathway may be manipulated.

The present crtO/Z gene clusters were selected for optimal production of astaxanthin. In another embodiment, the present genes may optionally be used to produce a variety of other carotenoids including, but are not limited to canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. The specific substrates for the present CrtO/Z enzymes are carotenoids having at least one β-ionone ring. Cyclic carotenoids are well known in the art and available commercially. In another embodiment, the cyclic carotenoid substrates include, but are not limited to, β-carotene, γ-carotene, zeaxanthin, rubixanthin, echinenone, and torulene. In one embodiment, the present crtOZ gene clusters are used to produce astaxanthin from β-carotene. In a further embodiment, the present crtOZ gene clusters are used to produce astaxanthin in a recombinant host cell engineered to produce β-carotene. Expression of β-carotene synthesis genes in recombinant host cells is well known in the art.

Vectors or cassettes useful for the transformation of suitable host cells are well known in the art. Typically the vector or cassette contains sequences directing transcription and translation of the relevant gene or gene cluster, a selectable marker, and sequences allowing autonomous replication or chromosomal integration. Suitable vectors comprise a region 5' of the gene or gene cluster which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the present coding sequences in the desired host cell are numerous and familiar to those skilled in the art. Virtually any promoter capable of driving these coding sequences is suitable for the present invention including, but not limited to: CYC1, HIS3, GAL1, GAL10, ADH1, PGK, PHO5, GAPDH, ADC1, TRP1, URA3, LEU2, ENO, TPI (e.g., useful for expression in *Saccharomyces*); AOX1 (e.g., useful for expression in *Pichia*); and lac, ara, tet, trp, $IP_L$, $IP_R$, T7, tac, and trc (e.g., useful for expression in *Escherichia coli*) as well as the amy, apr, npr promoters and various phage promoters useful for expression in, e.g., *Bacillus*. Additionally, the deoxy-xylulose phosphate synthase or methanol dehydrogenase operon promoter (Springer et al., *FEMS Microbiol Lett* 160:119–124 (1998)), the promoter for polyhydroxyalkanoic acid synthesis (Foellner et al., *Appl. Microbiol. Biotechnol.* 40:284–291 (1993)), promoters identified from native plasmids in methylotrophs (EP 296484), Plac (Toyama et al., *Microbiology* 143:595–602 (1997); EP 62971), Ptrc (Brosius et al., *Gene* 27:161–172 (1984)), promoters identified from methanotrophs (PCT/US03/33698), and promoters associated with antibiotic resistance [e.g., kanamycin (Springer et al., supra; Ueda et al., *Appl. Environ. Microbiol.* 57:924–926 (1991)), chloramphenicol, or tetracycline (U.S. Pat. No. 4,824,786)] are suitable for expression in C1 metabolizers.

It may be necessary to include an artificial ribosomal binding site ("RBS") upstream of the gene(s) to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene or gene cluster into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene(s) and whether the gene(s) are plasmid-borne or integrated into the genome of the host cell; 4.) the final cellular location of the synthesized foreign protein(s); 5.) the efficiency of translation in the host organism; 6.) the intrinsic stability of the cloned gene protein(s) within the host cell; and 7.) the codon usage within the cloned gene(s), such that its frequency approaches the frequency of preferred codon usage of the host cell. Each of these types of modifications are encompassed in the present invention, as means to further optimize expression of the present crtOZ genes.

Finally, to promote accumulation of astaxanthin, it may be necessary to reduce or eliminate the expression of certain genes in the target pathway or in competing pathways that may serve as sinks for energy or carbon. Alternatively, it may be useful to over-express various genes upstream of desired carotenoid intermediates to enhance production. Methods of manipulating genetic pathways for the purposes described above are common and well known in the art.

For example, once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene(s). Similarly, in some cases the native or endogenous promoter may be modified to increase gene/gene cluster expression. For example, endogenous promoters can be altered in vivo by mutation, deletion, and/or substitution (U.S. Pat. No. 5,565,350; Zarling et al., PCT/US93/03868).

Alternatively, where the sequences of the genes to be disrupted are known, one of the most effective methods for gene down-regulation is targeted gene disruption, where foreign DNA is inserted into a structural gene so as to disrupt transcription. This can be affected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617–4622 (1989); Balbas et al., *Gene*, 136:211–213 (1993); Gueldener et al., *Nucleic Acids Res.*, 24:2519–2524 (1996); and Smith et al., *Methods Mol. Cell. Biol.*, 5:270–277(1996)).

Antisense technology is another method of down-regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA encoding the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.* 36: 227–234 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see, for example: The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the carotenoid biosynthetic pathway by any one of the methods described above. For example, a number of genes encoding enzymes in the carotenoid pathway (crtE, crtX), crtY, crtI, crtB, crtZ, crtN, crtM, crtN1, crtN2, ald, sqs, etc.) are known, leading to the production of the desired carotenoid. Thus, it may also be useful to up-regulate the initial condensation of 3-carbon compounds (pyruvate and D-glyceraldehyde 3-phosphate) to increase the yield of the 5-carbon compound D-1-deoxyxylulose-5-phosphate (mediated by the dxs gene). This would increase the flux of carbon entering the carotenoid biosynthetic pathway and permit increased production of astaxanthin. Alternatively (or in addition to), it may be desirable to knockout one ore more of the crtN1, ald, or crtN2 genes leading to the synthesis of $C_{30}$ carotenoids, if the microbial host is capable of synthesizing these types of compounds. For example, an optimized *Methylomonas* sp. 16a strain has been created containing a knockout of the native $C_{30}$ pathway, creating a non-pigmented strain suitable for engineering $C_{40}$ carotenoid predution (U.S. Ser. No. 60/527,083; hereby incorporated by reference).

Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Industrial Production of Astaxanthin Using Recombinant Microorganisms

Where commercial production of astaxanthin is desired using the present crtOZ genes, a variety of culture methodologies may be applied. For example, large-scale production of the desired products (i.e. carotenoids and/or carotenoids biosynthesis enzymes) may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Brock (supra) or Deshpande (supra).

Commercial production of astaxanthin may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as methane or methanol, for which metabolic conversion into key biochemical intermediates has been demonstrated (U.S. Ser. No. 09/941,947; hereby incorporated by reference). In one embodiment, the carbon substrate is selected from the group consisting of methane and methanol and the recombinant host organisms is a methylotroph or a methanotroph. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

*Methylotrophs* and *Methylomonas* sp. 16a as Microbial Hosts

Although a number of carotenoids have been produced from recombinant microbial sources [e.g., *E. coli* and *Candida utilis* for production of lycopene (Farmer, W. R. and Liao, J. C., *Biotechnol. Prog.*, 17: 57–61 (2001); Wang et al., *Biotechnol Prog.*, 16: 922–926 (2000); Misawa, N. and Shimada, H., *J. Biotechnol.*, 59: 169–181 (1998); Shimada et al., *Appl. Environm. Microbiol.*, 64:2676–2680 (1998)]; *E. coli, Candida utilis* and *Pfaffia rhodozyma* for production of β-carotene (Albrecht et al., *Biotechnol. Lett.*, 21: 791–795 (1999); Miura et al., *Appl. Environm. Microbiol.*, 64:1226–1229 (1998); U.S. Pat. No. 5,691,190); *E. coli* and *Candida utilis* for production of zeaxanthin (Albrecht et al., supra; Miura et al., supra; *E. coli* and *Phaffia rhodozyma* for production of astaxanthin (U.S. Pat. No. 5,466,599; U.S. Pat. No. 6,015,684; U.S. Pat. No. 5,182,208; U.S. Pat. No. 5,972,642); see also: U.S. Pat. No. 5,656,472, U.S. Pat. No. 5,545,816, U.S. Pat. No. 5,530,189, U.S. Pat. No. 5,530,188, U.S. Pat. No. 5,429,939, and U.S. Pat. No. 6,124,113), these methods of producing carotenoids using various combinations of different crt genes suffer from low yields and reliance on relatively expensive feedstocks. Thus, it would be desirable to identify a method that produces high yields of carotenoids in a microbial host from an inexpensive feedstock.

There are a number of microorganisms that utilize single carbon substrates as their sole energy source. Such microorganisms are referred to herein as "C1 metabolizers". These organisms are characterized by the ability to use carbon substrates lacking carbon to carbon bonds as a sole source of energy and biomass. These carbon substrates include, but are not limited to: methane, methanol, formate, formaldehyde, formic acid, methylated amines (e.g., mono-, di- and tri-methyl amine), methylated thiols, carbon dioxide, and various other reduced carbon compounds which lack any carbon—carbon bonds. In a particular embodiment, the carbon substrate is methanol and/or methane.

All C1 metabolizing microorganisms are generally classified as methylotrophs. Methylotrophs may be defined as any organism capable of oxidizing organic compounds that do not contain carbon—carbon bonds. However, facultative methylotrophs, obligate methylotrophs, and obligate methanotrophs are all various subsets of methylotrophs. Specifically:

Facultative methylotrophs have the ability to oxidize organic compounds which do not contain carbon—carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1-Compounds.*, [Int. Symp.], 7th (1993), pp 285–302. Murrell, J. Collin and Don P. Kelly, eds. Intercept: Andover, UK; Madigan et al., *Brock Biology of Microorganisms*, 8th ed., Prentice Hall: Upper Saddle River, N.J. (1997)).

Obligate methylotrophs are those organisms that are limited to the use of organic compounds that do not contain carbon—carbon bonds for the generation of energy.

Obligate methanotrophs are those obligate methylotrophs that have the distinct ability to oxidize methane.

Additionally, the ability to utilize single carbon substrates is not limited to bacteria but extends also to yeasts and fungi. A number of yeast genera are able to use single carbon substrates as energy sources in addition to more complex materials (i.e., the methylotrophic yeasts).

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these hardships, many methanotrophs contain an inherent isoprenoid pathway which enables these organisms to synthesize pigments and provides the potential for one to envision engineering these microorganisms for production of other non-endogenous isoprenoid compounds. Since methanotrophs can use single carbon substrates (i.e., methane and/or methanol) as an energy source, it could be possible to produce carotenoids at low cost in these organisms. Examples wherein a methanotroph was engineered for production of β-carotene are described in U.S. Ser. No. 09/941,947 and U.S. Ser. No. 60/527,083.

In the present invention, methods are provided for the expression of genes involved in the biosynthesis of astaxanthin in microorganisms that are able to use single carbon substrates as a sole energy source. The host microorganism may be any C1 metabolizer that has the ability to synthesize β-carotene as a metabolic precursor for astaxanthin. More specifically, facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Specific methylotrophic yeasts useful in the present invention include, but are not limited to: *Candida, Hansenula, Pichia, Torulopsis*, and *Rhodotorula*. And, exemplary methanotrophs are included in, but are not limited to, the genera *Methylomonas, Methylobacter, Methylococcus, Methylosinus, Methylocyctis, Methylomicrobium*, and *Methanomonas*.

Of particular interest in the present invention are high growth obligate methanotrophs having an energetically favorable carbon flux pathway. For example, a specific strain of methanotroph has been discovered having several pathway features that makes it particularly useful for carbon flux manipulation. This strain is known as *Methylomonas* sp. 16a (ATCC PTA 2402) (U.S. Pat. No. 6,689,601; hereby incorporated by reference); and, this particular strain and other related methylotrophs are preferred microbial hosts for expression of the gene products of this invention, useful for the production of $C_{40}$ carotenoids (U.S. Ser. No. 09/941,947).

*Methylomonas* sp. 16a naturally produces $C_{30}$ carotenoids. Odom et al. have reported that expression of $C_{40}$ carotenoid genes in *Methylomonas* 16a produced a mixture of $C_{30}$ and $C_{40}$ carotenoids (U.S. Ser. No. 09/941,947). Several of the genes involved in $C_{30}$ carotenoid production in this strain have been identified including (but not limited to) the crtN1, ald, crtN2, and crtN3 genes. Disruption of the crtN1/ald genes or the promoter driving expression of the crtN1/ald/crtN2 gene cluster created various non-pigmented mutants ("white mutants") more suitable for $C_{40}$ carotenoid production (U.S. Ser. No. 60/527,083, hereby incorporated by reference). For example, a non-pigmented *Methylomonas* sp. 16a strain "MWM1000" was created by disrupting the ald and crtN1 genes (U.S. Ser. No. 60/527,083).

Transformation of C1 Metabolizing Bacteria

Techniques for the transformation of C1 metabolizing bacteria are not well developed, although general methodology that is utilized for other bacteria, which is well known to those of skill in the art, may be applied. Electroporation has been used successfully for the transformation of: *Methylobacterium extorquens* AM1 (Toyama, H., et al., *FEMS Microbiol. Lett.*, 166:1–7 (1998)), *Methylophilus methylotrophus* AS1 (Kim, C. S., and Wood, T. K., *Appl. Microbiol. Biotechnol.*, 48: 105–108 (1997)), and *Methylobacillus* sp. strain 12S (Yoshida, T., et al., *Biotechnol. Lett.*, 23: 787–791 (2001)). Extrapolation of specific electroporation parameters from one specific C1 metabolizing utilizing organism to another may be difficult, however, as is well to known to those of skill in the art.

Bacterial conjugation, relying on the direct contact of donor and recipient cells, is frequently more readily amenable for the transfer of genes into C1 metabolizing bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in onT; 2.) A single-strand DNA is released to the recipient through a pore or pilus structure; 3.) A DNA relaxase enzyme cleaves the double-strand DNA at onT and binds to a release 5' end (forming a relaxosome as the intermediate structure); and 4.) Subsequently, a complex of auxiliary proteins assemble at onT to facilitate the process of DNA transfer.

Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an onT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C metabolizing bacteria include the work of: Stolyar et al. (*Mikrobiologiya* 64(5): 686–691 (1995)); Motoyama et al. (*Appl. Micro. Biotech.* 42(1): 67–72 (1994)); Lloyd et al. (*Archives of Microbiology* 171(6): 364–370 (1999)); U.S. Ser. No. 09/941,947; U.S. Ser. No. 60/527,083; and U.S. Ser. No. 60/527,877, hereby incorporated by reference.

Recombinant Expression of crtOZ—Plants

Plants and algae are also known to produce carotenoid compounds, such as astaxanthin. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina, Haemotacoccus*, and *Dunalliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence(s). Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al.,

*The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.*, 618 (1–2) (1993) 133–145), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247–253 (1989)), signal sequences or sequences encoding endoplasmic reticulum localization (Chrispeels, J. J., *Ann. Rev. Plant Phys. Plant Mol. Biol.*, 42:21–53 (1991)), or nuclear localization signals (Raikhel, N., *Plant Phys.*, 100: 1627–1632 (1992)) added and/or with targeting sequences that are already present removed. While the references cited give examples of each of these, the list is not exhaustive and more targeting signals of utility may be discovered in the future that are useful in the invention.

In Vitro Bio-Conversion of Carotenoids

Alternatively, it is possible to carry out the bioconversions of the present application in vitro. Where substrates for the present CrtO ketolase and CrtZ hydroxylase are not synthesized by the host cell, it will be possible to add the substrate(s) exogenously. In this embodiment the suitable carotenoid substrate may be solubilized with mild detergent (e.g., DMSO) or mixed with phospholipid vesicles. To assist in transport into the cell, the host cell may optionally be permeabilized with a suitable solvent such as toluene. Methods for this type of in-vitro bio-conversion of carotenoid substrates has basis in the art (see for example: Hundle, B. S., et al., *FEBS*, 315:329–334 (1993); and Bramley, P. M., et al., *Phytochemistry*, 26:1935–1939 (1987)).

Protein Engineering CrtO Ketolases and CrtZ Hydroxylases

The present nucleic acid fragments encoding the CrtO ketolases and CrtZ hydroxylases were protein engineered by subjecting the instand genes to mutational conditions using error-prone PCR ((Melnikov et al., *Nucleic Acids Research*, 27(4):1056–1062 (1999); Leung et al., *Techniques*, 1:11–15 (1989); and Zhou et al., *Nucleic Acids Res.*, 19:6052–6052 (1991)). It is contemplated that the present crtOZ genes may be further engineered to produce gene products having further enhanced or altered activity. Alternate methods of mutating genes and selecting for mutants are known including, but not limited to: 1.) site-directed mutagenesis (Coombs et al., *Proteins* (1998), pp 259–311, 1 plate. Angeletti, Ruth Hogue, Ed., Academic: San Diego, Calif.); and 2.) "gene-shuffling" (U.S. Pat. No. 5,605,793; U.S. Pat. No. 5,811,238; U.S. Pat. No. 5,830,721; and U.S. Pat. No. 5,837,458 or any similar means of promoting recombinogenic activity between nucleic acids (see for example Tang et al., U.S. Ser. No. 10/374,366; hereby incorporated by reference)).

The method of gene shuffling has the advantage of facile implementation, high rate of mutagenesis, and ease of screening. The process of gene shuffling involves the restriction endonuclease cleavage of a gene of interest into fragments of specific size in the presence of additional populations of DNA fragments having regions of similarity or difference to the gene of interest. This pool of fragments will then be denatured and reannealed to create a mutated gene. The mutated gene is then screened for altered activity.

The present sequences may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments that are not hybridizable to the instant sequences may also be added. Typically these additional fragment populations are added in about a 10 to 20-fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably, the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably, the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Maniatis, supra).

Furthermore, a hybrid protein can be assembled by fusion of functional domains using the gene shuffling (exon shuffling) method (Nixon et al., *Proc. Natl. Acad. Sci.*, 94:1069–1073 (1997)). The functional domain of the instant gene(s) can be combined with the functional domain of other genes to create novel enzymes with desired catalytic function.

In addition to the methods exemplified above (which are designed to directly mutagenize the crtOZ gene clusters encoding CrtO ketolases and CrtZ hydroxylases), traditional methods of creating mutants could be utilized for the purposes described herein. For example, wild-type cells having carotenoid ketolase and carotenoid hydroxylase activity may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm, where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible; but this range is generally not as effective as the short wave UV light, unless used in conjunction with various activators (such as psoralen dyes) that interact with the DNA. Likewise, mutagenesis with chemical agents is also effective for generating mutants and commonly used substances include chemicals that affect nonreplicating DNA (such as $HNO_2$ and $NH_2OH$), as well as agents that affect replicating DNA (such as acridine dyes, notable for causing frameshift mutations). Specific methods for creating mutants using radiation or chemical agents are well documented in the art. See, for example, Brock (supra) or Deshpande (supra).

Method of gene mutation preferred herein involve Error Prone PCR. Accordingly, the present crtOZ genes were simultaneously mutated (i.e. exposed to mutational conditions) using error-prone PCR to create gene clusters encoding CrtO/CrtZ enzymes having the ability to produce astaxanthin. In one embodiment, a method to produce match carotenoid ketolase and carotenoid hydroxylase enzymes exhibiting improved production of astaxanthin is provided. The method is comprised of simultaneously mutating (or at least exposing the starting genes to mutational conditions) any carotenoid hydroxylase (CrtZ or CrtR) and carotenoid ketolase (CrtO, CrtW/bkt) using any well known protein engineering techniques (error-prone PCR, gene shuffling, random mutagenesis, etc.) to produce hydroxylase/ketolase combinations having an improved ability to produce astaxanthin. The resulting ketolase/hydroxylase gene clusters are then simultaneously transformed and expressed in recombinant host cells capable of producing β-carotene. Transformants exhibiting improved astaxanthin production (assessed either by visually screening or any common analytical method such as HPLC) are then evaluated for mutations accounting for the structural changes responsible for improved astaxanthin production. The matched carotenoid ketolase/carotenoid hydroxylase genes exhibiting improvements in astaxanthin production can be selected as the "starting genes" for additional rounds of protein engineering. In an optional embodiment, the crtO and crtZ genes can be individually mutated and then coexpressed in a recombinant host cell capable of producing β-carotene in order to evaluate the combination's ability to produce astaxanthin. However, simultaneous mutation and coexpression of the mutated genes is preferable, thereby being able to select (in a single step) crtOZ gene clusters having optimal astaxanthin synthesizing activity.

Irrespective of the method of mutagenesis, the crtOZ genes may be evolved such that the enzymes have an increase in astaxanthin synthesis activity. The increase in astaxanthin synthesis activity can be measured using a variety of techniques known in the art. In the present invention, a simple measurement of astaxanthin production in the presence of excess substrate (i.e. β-carotene) under identical reaction conditions will typically be suitable to identify enzymes capable of providing a higher percentage yield of a astaxanthin.

EXAMPLES

General Methods:

Procedures required for PCR amplification, DNA modifications by endo- and exonucleases for generating desired ends for cloning of DNA, ligation, and bacterial transformation are well known in the art. Standard molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring, N.Y., 1984 and by Ausubel et al., *Current Protocols in Molecular Biology*; Greene Publishing and Wiley-Interscience; 1987.

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C., 1994 or by Brock, T. D.; *Biotechnology: A Textbook of Industrial Microbiology*, 2nd ed.; Sinauer Associates: Sunderland, Mass., 1989. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

PCR reactions were run on GeneAMP PCR System 9700 using Amplitaq or Amplitaq Gold enzymes (PE Applied Biosystems, Foster City, Calif.), unless otherwise specified. The cycling conditions and reactions were standardized according to the manufactures' instructions.

The meaning of abbreviations is as follows: "min"means minute(s), "h" means hour(s), "μL" means microliter, "mL" means milliliters, "L" means liters, "cm" means centimeters, "nm" means nanometers, "mM" means millimolar, "kB" means kilobases, and "kV" means kilovolts.

Example 1

Selection of the crtOZ Plasmid for Protein Engineering Construction of Two Plasmids Containing Different crtOZ Genes The crtO gene isolated from *Rhodococcus erythropolis* AN12 has previously been engineered (U.S. Ser. No. 60/577,970) to increase the ketolase activity. One of the mutants, crtO-SHU001, produced over 90% canthaxanthin in *E. coli* when coexpressed with β-carotene synthesis genes. This crtO was chosen to pair with crtZ for astaxanthin production. The crtO-SHU001 gene (SEQ ID NOs: 1 and 3) was PCR-amplified from pDCQ320-SHU001 plasmid DNA (U.S. Ser. No. 60/577,970), using forward primer crtO-SHU001-F 5'-

ACTAGTAAGGAGGAATAAACCATGAGCGCA-3' (SEQ ID NO: 3) and reverse primer crtO-SHU001-R 5'-TGTACAGCTAGCTCACGACGCG CTCGAACGACG-CAT-3' (SEQ ID NO: 4). Underlined are restriction sites for Spe I, Nhe I and BrsG I. The ~1.6 kb PCR product was gel purified and cloned into pTrcHis2-Topo vector, resulting in plasmid pDCQ353. The ~1.6 kb SpeI I/BrsG I fragment of pDCQ353 DNA containing the crtO-SHU001 gene was cloned to the pDCQ334 plasmid (pDCQ334 is a plasmid comprised of a crtWZEidiYIB gene cluster prepared by cloning the codon optimized (for *Methylomonas* 16a) *Agrobacterium aurantiacum* crtWZ genes upstream of the *Pantoea agglomerans* DC404 β-carotene gene cluster; see U.S. Ser. No. 60/527,083 and U.S. Ser. No. 10/808,807; herby incorporated by reference) digested with SpeI/BsrGI to remove crtWZ, which resulted in pDCQ354 containing crtOEidiYIB. *E. coli* cells containing pDCQ354 were orange and produced almost exclusively canthaxanthin.

The crtZ genes from two different sources were compared to see how well they function with the CrtO (encoded by crtO-SHU001) for astaxanthin production. The crtZ from DC263 (U.S. Ser. No. 60/601,947; SEQ ID NOs: 5 and 6) was amplified using primers crtZ-263_F2: 5'-TCTAGAAAGGAGGAATAAACCATGTCCTGGCCGA CGATGATC-3' (SEQ ID NO: 7) and crtZ-263_R2: 5'-ACTAGTCAGGCGCCGTTGCTGGATGA-3' (SEQ ID NO: 8). The 507 bp PCR product was cloned into pTrcHis2-TOPO vector resulting pDCQ352. The crtZ from DC260 (U.S. Ser. No. 10/808,979; SEQ ID NOs: 9 and 10) was amplified using forward primer crtZ-DC260-F 5'-ACTAGTAAGGAGGAATAAACCATGCTCTGGTTAT GGAACGTGC-3' (SEQ ID NO: 11) and reverse primer crtZ-DC260-R 5'-ACTAGTTCACTTCGCGTGT GTCTCGTC-3' (SEQ ID NO: 12). The 561 bp PCR product was cloned into pTrcHis2-Topo vector, resulting in plasmid pDCQ355. Underlined are restriction sites for Spe I and XbaI. The XbaI-SpeI fragment containing DC263 crtZ from pDCQ352 and the SpeI fragment containing DC260 crtZ from pDCQ355 were cloned into the SpeI site of pDCQ354, resulting pDCQ356 and pDCQ357, respectively.

Carotenoid Analysis of Cells Containing pDCQ356 or PDCQ357

HPLC analysis was performed on cells containing these plasmids. Cells were pelleted by centrifugation at 4000 g for 15 min, and the cell pellets were extracted with 1–2 mL acetone. The extraction was dried under nitrogen and redissolved in 0.5 mL of 50% acetone+50% methanol. The extraction was filtered with an Acrodisc® CR25 mm syringe filter (Pall Corporation, Ann Arbor, Mich.) for HPLC analysis using an Agilent Series 1100 LC/MSD SI (Agilent, Foster City, Calif.).

Samples (20 µL) were loaded onto a 150 mm×4.6 mm ZORBAX C18 (3.5 µm particles) column (Agilent Technologies, Inc.). The column temperature was kept at 40° C. The flow rate was 1 mL/min, while the solvent running program used was 0–2 min: 95% Buffer A and 5% Buffer B;

2–10 min: linear gradient from 95% Buffer A and 5% Buffer B to 60% Buffer A and 40% Buffer B;

10–12 min: linear gradient from 60% Buffer A and 40% Buffer B to 50% Buffer A and 50% Buffer B;

12–18 min: 50% Buffer A and 50% Buffer B; and,

18–20 min: 95% Buffer A and 5% Buffer B.

Buffer A was 95% acetonitrile and 5% dH₂O; Buffer B was 100% tetrahydrofuran (THF). The mass spectrometer was scanned from 250 to 900 e/z in APCI (Atmospheric Pressure Chemical Ionization) mode with the fragmentation voltage at 70 V. No astaxanthin was produced in *E. coli* containing either of the plasmids. These *E. coli* cells were yellow and produced predominantly zeaxanthin and trace amounts of ketocarotenoids. These two plasmids were transferred into *Methylomonas* sp. 16a (non-pigmented MWM1200 strain; U.S. Ser. No. 60/527,083; hereby incorporated by reference) by tri-parental conjugation. Astaxanthin was not produced in *Methylomonas* tranformants containing either plasmid. *Methylomonas* containing pDCQ356 produced carotenoids containing 69% zeaxanthin and 26% adonixanthin. *Methylomonas* containing pDCQ357 produced carotenoids containing 80% zeaxanthin and 11% adonixanthin. Since higher amount of adonixanthin intermediate was produced by pDCQ356, this plasmid pDCQ356 was chosen for protein engineering to produce astaxanthin.

Example 2

Making Mutant Libraries

Error-Prone PCR:

The plasmid pDCQ356 was used as a template for error-prone PCR. The insert containing the crtOZ genes (SEQ ID NO: 1 and SEQ ID NO: 5; respectively) can be removed from the construct using BsrG I and Spe I digestion. A random mutant library targeting the crtOZ genes was made using error-prone PCR. The following primers were used to amplify the inserts by error-prone PCR:

334F1 5'-GCA GCG TGC AGC TCA TGC AGT TC-3' (SEQ ID NO: 13)

334r1 5'-CCA GAC CGT TCA GCT GGA TAT TAC-3' (SEQ ID NO: 14)

A Clontech mutagenesis kit (Clontech Laboratories, Inc., Palo Alto, Calif.) was used for performing error-prone PCR. The following condition was used for preparing error-prone PCR reaction mixture:

TABLE 1

| Conditions for Error-prone PCR using Clontech Mutagenesis Kit | |
|---|---|
| | Volumes (µL) |
| PCR grade water | 37 |
| 10x AdvanTaq Plus Buff. | 5 |
| MnSO₄ (8 mM) | 3 |
| dGTP (2 mM) | 1 |
| 50x Diversify dNTP Mix | 1 |
| Primer mix | 0 |
| Template DNA | 1 |
| AdvanTaq Plus Polym. | 1 |

The thermal cycling reaction was carried out according to the manufacturer's instructions. The PCR products were digested with BsrG I/Spe I.

Mutant Library Construction:

To prepare the vector, the template plasmid (pDCQ356) was digested with BsrG I and Spe I to remove the insert. The digested vector was purified from the agarose gel. The BsrG I/Spe I-digested error-prone PCR products were then ligated with the BsrG I/Spe I-digested vectors. After ethanol precipitation, the ligation mixture was ready for the transformation.

The ligation mixture was first transformed into Electroporation-Competent *E. coli* 10G cells (Lucigen Corp., Middleton, Wis.) by electroporation. The cells were plated onto LB plates in the presence of kanamycin and incubated overnight at 37° C. The mutant colonies were ready for high-throughput screening.

DNA Sequence Analysis of the Mutant Libraries:

Ten mutant colonies from each library were randomly picked for DNA sequencing analyses. The mutant genes were sequenced on an ABI 377 automated sequencer (Applied Biosystems, Foster City, Calif.), and the data managed using Vector NTI program (InforMax, Inc., Bethesda, Md.). Most of the mutations were base substitutions, the frequency of deletions and insertions in the mutant libraries was very low. Various types of base substitution were present in these mutants, indicating there was no bias for the mutation type. The mutation rate was approximately 1–5 point mutations per kB.

Example 3

Screening the Mutant Libraries and Identifying the Hits

The color of cells containing pDCQ356 was light yellow. The color of the cells producing astaxanthin is red-orange. The cells that make different percentages of astaxanthin show slightly different levels of pigmentation. Therefore, the mutant colonies that produce different amounts of astaxanthin can be distinguished visually. Approximately 10,000–20,000 mutant colonies from the mutant library were screened visually. Nine putative hits were streaked on Agar plates.

A follow-up confirmation assay was performed by HPLC analysis. *E. coli* 10G cells containing pDCQ356 and its mutant derivatives were grown in 25 ml LB with 50 µg/mL kanamycin at 30° C.; shaking for two days. Cells were harvested by centrifugation and extracted with 50% acetone and 50% methanol. HPLC analysis of the carotenoids was performed as described in Example 1. Two of the nine crtOZ mutants produced astaxanthin as shown in Table 2.

TABLE 2

HPLC Confirmation Analysis Results

| Carotenoids | pDCQ356 (starting genes) | pDCQ356M4003 | pDCQ356M4005 |
| --- | --- | --- | --- |
| astaxanthin | 0% | 26% | 20% |
| adonixanthin | 5% | 4% | 31% |
| zeaxanthin | 80% | <1% | 8% |
| adonirubin | 0% | 21% | 12% |
| canthaxanthin | 0% | 44% | 18% |

The data in Table 2 showed that the percentage yield of carotenoids. The starting construct (pDCQ356) did not make any astaxanthin. However, two mutants made 20–26% of astaxanthin and other intermediates. The rest of putative hits did not make any astaxanthin, but produced canthaxanthin and echinenone.

Example 4

DNA Sequence Analysis of the Mutant Genes

The mutant genes were sequenced on an ABI377 automated sequencer (Applied Biosystem, Foster City, Calif.), and the data managed using Vector NTI program (InforMax, Inc., Bethesda, Md.). Analysis of the mutants, followed by comparison with the starting genes, indicated that the mutant genes contained the following point mutations:

TABLE 3

DNA sequence analysis of mutant genes

| Strain | Starting Gene(s)/Mutations |
| --- | --- |
| 356M4003 (SEQ ID NOs. 15–19) | crtO-SHU001: GCA(Ala16) to GCT(Ala) GGG(Gly203) to GGA(Gly) CTC(Leu305) to CTT(Leu) CrtZ DC263: CTG(Leu53) to CCG(Pro) ACG(Thr84) to ACT(Thr) ACA(Thr128) to ACC(Thr) |
| 356M4005 (SEQ ID NOs. 20–24) | crtO-SHU001: GCA(Ala190) to GTA(Val) GTT(Val277) to GTC(Val) CTC(Leu305) to CTT(Leu) CrtZ DC263: TTC(Phe91) to TCC(Ser) GTG(Val140) to GGG(Gly) |

Except for the silent mutations, all the mutations were the amino acid substitutions.

Example 5

Performance of Mutant Genes in *Methylomonas*

Plasmid pDCQ356 and the mutant derivatives were transferred into *Methylomonas* sp. 16a (MWM1200 strain; U.S. Ser. No. 60/527,083) by tri-parental conjugal mating. The *E. coli* helper strain containing pRK2013 (ATCC No. 37159) and the *E. coli* XL1BlueMRF' donor strains containing the plasmid were each grown overnight in LB medium containing kanamycin (50 µg/mL), washed three times in LB, and resuspended in a volume of LB representing approximately a 60-fold concentration of the original culture volume.

The *Methylomonas* 16a recipient MWM1200 was grown using the general conditions described in WO 02/18617. Briefly, this involves growing *Methylomonas* 16a in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking.

Nitrate Medium for *Methylomonas* 16A

Nitrate liquid medium, also referred to herein as "defined medium" or "BTZ-3" medium is comprised of various salts mixed with Solution 1 as indicated below (Tables 4 and 5) or where specified the nitrate is replaced with 15 mM ammonium chloride. Solution 1 provides the composition for 100-fold concentrated stock solution of trace minerals.

TABLE 4

Solution 1*

| | MW | Conc. (mM) | g per L |
| --- | --- | --- | --- |
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |

TABLE 4-continued

Solution 1*

| | MW | Conc. (mM) | g per L |
|---|---|---|---|
| Na$_2$MoO$_4$ × 2H$_2$O | 241.95 | 0.04 | 0.01 |
| NiCl$_2$ × 6H$_2$O | 237.7 | 0.77 | 0.184 |

*Mix the gram amounts designated above in 900 mL of H$_2$O, adjust to pH = 7, and add H$_2$O to an end volume of 1 L. Keep refrigerated.

TABLE 5

Nitrate liquid medium (BTZ-3)**

| | MW | Conc. (mM) | g per L |
|---|---|---|---|
| NaNO$_3$ | 84.99 | 10 | 0.85 |
| KH$_2$PO$_4$ | 136.09 | 3.67 | 0.5 |
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7) | 238.3 | | 50 mL |
| Solution 1 | | | 10 mL |

**Dissolve in 900 mL H$_2$O. Adjust to pH = 7, and add H$_2$O to give 1 L.

For agar plates: Add 15 g of agarose in 1 L of medium, autoclave, let cool down to 50° C., mix, and pour plates.

The standard gas phase for cultivation contains 25% methane in air. Using these conditions, the recipient was cultured for 48 h in BTZ-3 medium, washed three times in BTZ-3, and resuspended in a volume of BTZ-3 representing a 150-fold concentration of the original culture volume.

The donor, helper, and recipient cell pastes were then combined in ratios of 1:1:2, respectively, on the surface of BTZ-3 agar plates containing 0.5% (w/v) yeast extract. Plates were maintained at 30° C. in 25% methane for 16–72 h to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Transconjugants were streaked onto BTZ-3 agar with kanamycin (50 µg/mL) for isolation.

For analysis of carotenoid composition, *Methylomonas* transconjugants were cultured in a 24-well blocks (Qiagen catalog no. 19583) with each well containing 1 mL BTZ-3 containing kanamycin (50 µg/mL). The block was covered with Airpore™ film (Qiagen) and incubated in an Anaero-Pack™ System (Mitsubishi Gas Chemical Co., Inc., Japan) filled with 25% methane as the sole carbon source. The AnaeroPack™ was shaking at 250 rpm for 2–3 days at 30° C. The cells were harvested by centrifugation and the pellets were extracted and carotenoid content was analyzed by HPLC, as described in Example 1. Table 6 summarized the results:

TABLE 6

| | HPLC analysis results | | |
|---|---|---|---|
| Carotenoids | pDCQ356 (starting genes) | pDCQ356M4003 | pDCQ356M4005 |
| astaxanthin | 0% | 5% | 37% |
| adonixanthin | 26% | <1% | 5% |
| zeaxanthin | 69% | <1% | <1% |
| adonirubin | 0% | 11% | 11% |
| canthaxanthin | 0% | 70% | 45% |

What is claimed is:

1. An nucleic acid molecule encoding at least one carotenoid ketolase and at least one carotenoid hydroxylase, said nucleic acid molecule comprising:
   a) a nucleic acid fragment encoding a carotenoid ketolase having an amino acid sequence selected from the group consisting of SEQ ID NO: 17 and SEQ ID NO: 22; and
   b) a isolated nucleic acid fragment encoding a carotenoid hydroxylase having an amino acid sequence selected from the group consisting of SEQ ID NO: 19 and SEQ ID NO: 24; or
   an isolated nucleic acid molecule completely complementary to the nucleic acid molecule comprising (a) and (b).

2. An isolated nucleic acid molecule encoding at least one carotenoid ketolase and at least one carotenoid hydroxylase, said nucleic acid molecule comprising:
   a) a nucleic acid fragment encoding a carotenoid ketolase having a nucleic acid sequence selected from the group consisting of SEQ ID NO: 16 and SEQ ID NO: 21; and
   b) a nucleic acid fragment encoding a carotenoid hydroxylase having a nucleic acid sequence selected from the group consisting of SEQ ID NO: 18 and SEQ ID NO: 23; or
   an isolated nucleic acid molecule completely complementary to the nucleic acid molecule comprising (a) and (b).

3. An isolated nucleic acid molecule encoding a carotenoid ketolase and a carotenoid hydroxylase, said isolated nucleic acid molecule comprising:
   a) a nucleic acid fragment encoding a carotenoid ketolase having the amino acid sequence as represented by SEQ ID NO: 17 and
   a nucleic acid fragment encoding a carotenoid hydroxylase enzyme having the amino acid sequence as represented by SEQ ID NO: 19; or
   (b) an isolated nucleic acid molecule completely complementary to the nucleic acid fragment of (a).

4. An isolated nucleic acid molecule encoding a carotenoid ketolase and a carotenoid hydroxylase, said isolated nucleic acid molecule comprising:
   a) a nucleic acid fragment encoding a carotenoid ketolase having the amino acid sequence as represented by SEQ ID NO: 21; and
   a nucleic acid fragment encoding a carotenoid hydroxylase enzyme having the amino acid sequence as represented by SEQ ID NO: 23; or
   b) an isolated nucleic acid molecule completely complementary to the nucleic acid fragment of (a).

5. An isolated and transformed host cell comprising the isolated nucleic acid molecule of any of claims 1 or 3.

6. The transformed host cell of claim 5 wherein the host cell is selected from the group consisting of bacteria, yeast, filamentous fungi, algae, and green plants.

7. The transformed host cell of claim 6 wherein the host cell is selected from the group consisting of *Aspergillus, Trichoderma, Saccharomyces, Pichia, Phaffia, Candida, Hansenula, Salmonella, Bacillus, Acinectorbacter, Zymomonas, Agrobacterium, Erythrobacter, Chloroborium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Methanomonas, Synechococcus, Anabeana, Thiobacillus, Methanobacterium, Klebsiella,* and *Myxococcus*.

8. The transformed host cell of claim 7 wherein the host cell is *Methylomonas* sp. 16a having the designation ATCC PTA 2402.

9. The transformed host cell of claim 6 where the host cell is selected from the group consisting of soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa,* L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

* * * * *